United States Patent [19]
Cook et al.

[11] Patent Number: 6,133,438
[45] Date of Patent: Oct. 17, 2000

[54] PROCESS FOR THE PREPARATION OF 2'-O-ALKYL PURINE PHOSPHORAMIDITES

[75] Inventors: Phillip Dan Cook, Carlsbad, Calif.; Daniel Peter Claude McGee, Boulder, Colo.; Charles John Guinosso, Vista, Calif.

[73] Assignee: Isis Pharmaceuticals, Inc., Carlsbad, Calif.

[21] Appl. No.: 09/165,680

[22] Filed: Oct. 2, 1998

Related U.S. Application Data

[62] Division of application No. 08/888,880, Jul. 7, 1997, Pat. No. 5,856,466, which is a division of application No. 08/410,002, Mar. 23, 1995, Pat. No. 5,646,265, which is a continuation of application No. 07/968,849, Oct. 30, 1992, abandoned, which is a continuation-in-part of application No. 07/967,267, Oct. 27, 1992, which is a continuation-in-part of application No. 07/918,362, Jul. 23, 1992, Pat. No. 5,506,351, and a continuation-in-part of application No. 07/854,634, filed as application No. PCT/US91/00243, Jan. 11, 1991, abandoned, and a continuation-in-part of application No. 07/463,358, Jan. 11, 1990, abandoned, and a continuation-in-part of application No. 07/566,977, Aug. 13, 1990, abandoned.

[51] Int. Cl.$^7$ .............................. C07H 21/00; C07H 19/06
[52] U.S. Cl. ..................................... 536/25.34; 536/26.71; 536/26.72; 536/27.81; 536/28.5; 536/28.51
[58] Field of Search ................................. 536/55.3, 26.71, 536/26.72, 27.81, 25.34, 28.5, 28.51

[56] References Cited

U.S. PATENT DOCUMENTS

| | | | |
|---|---|---|---|
| 4,725,677 | 2/1988 | Köster et al. | 536/25.34 |
| 5,214,135 | 5/1993 | Srivastava et al. | 536/26.7 |
| 5,466,786 | 11/1995 | Buhr et al. | 435/26.26 |
| 5,506,351 | 4/1996 | McGee | 536/55.3 |
| 5,646,265 | 7/1997 | McGee | 536/25.34 |
| 5,658,731 | 8/1997 | Sproat et al. | 435/6 |

FOREIGN PATENT DOCUMENTS

| | | |
|---|---|---|
| 0 269 574 A2 | 6/1988 | European Pat. Off. . |
| 0378518 | 7/1990 | European Pat. Off. . |
| 4110085 | 10/1992 | Germany . |

OTHER PUBLICATIONS

Iribarren et al., "2'O–Alkyl Oligoribonucleotides as Antisense Probes", *Proc. Natl. Acad. Sci. USA*, 1990, 87, 7747–7751.

Berner et al., "Studies on the role of tetrazole in the activation of phosphoramidites", *Nucl. Acids Res.*, 1989, 17, 853–864.

Cotton et al., "2'–O–methyl, 2'–O–ethyl oligoribonucleotides and phosphorothioate oligodeoxyribonucleotides as inhibitors of the in vitro U7 snRNP–dependent mRNA processing event", *Nucl. Acids Res.*, 1991, 19, 2629–2635.

Dahl et al., "Mechanistic studies on the phosphoramidite coupling reaction in oligonucleotide synthesis. I. Evidence for nucleophilic catalysis by tetrazole and rate variations with the phosphorus substitutents", *Nucl. Acids Res.*, 1987, 15, 1729–1743.

Inoue et al., "Synthesis and hybridization studes on two complementary nona(2'–O–methyl) ribonucleotides", *Nucl. Acids Res.*, 1987, 15, 6131–6148.

Nielson et al., "Thermal Instability of Some Alkyl Phosphorodiamidites", *J. Chem. Res.*, 1986, 26–27.

Robins et al., "Nucleic Acid Related Compounds. 12. The Facile and High–Yield Stannous Chloride Catalyzed Monomethylation of the Cis–Glycol System of Nucleosides by Diazomethane", *J. Org. Chem.*, 1974, 39, 1891–1899.

Robins, "Nucleic acid related compounds. 36. Synthesis of the 2'–O–methyl and 3'–O–methyl ethers of guanosine and 2–aminoadenosine and correlation of 0'–methylnucleoside $^{13}$C nmr spectral shifts", *Can. J. Chem.*, 1981, 59, 3360–3364.

Singer et al., "Alkylation of Ribose in RNA Reacted with Ethylnitrosourea at Neutrality", *Biochem.*, 1976, 15(23), 5052–5057.

Sproat et al., "New synthetic routes to protected purine 2'–O–methylriboside–3'–O–phosphoramidites using a novel alkylation procedure", *Nucl. Acids Res.*, 1990, 18, 41–49.

Sproat et al., "2'–O–Methyloligoribonucleotides: synthesis and applications", *Oligonucleotides and Analogs A Practical Approach*, Eckstein (ed.), IRL Press, Oxford, 1991, 49–86.

Sproat et al., "New synthetic routes to synthons suitable for 2'–O–allyloligoribonucleotide assembly", *Nucl. Acids Res.*, 1991, 19, 733–738.

Wagner et al., "A simple procedure for the preparation of protected 2'–O–methyl or 2'–O–ethyl ribonucleosides–3'–O–phosphoramidites", *Nucl. Acids Res.*, 1991, 19, 5965–5971.

Wagner et al., "Preparation and synthetic Utility of Some Organotin Derivatives of Nucleosides", *J. Org. Chem.*, 1974, 39(1), 24–30.

Chavis et al., "Synthesis of 2',3'–Differentiated Ribonucleosides via Lycosylation Reactions with 2'–O–TBDMS Ribofuranose Derivatives. A. Pyrimidine Series", *J. Org. Chem.*, 1982, 47, 202–206.

Divakar et al., "Reaction Between 2,2'–Anhydro–1–β–p–arabinofuranosyluracil and Thiolate Ions", *J. Chem. Soc. Perkin Trans.*, 1982, 1625–1628.

Khurshid, M. et al., "The Unique Conformational Stability of Poly 2'–O–Ethyladenylic Acid", *FEBS Letts.*, 1972, 28(1), 25–28.

OTHER PUBLICATIONS

*Primary Examiner*—James O. Wilson
*Attorney, Agent, or Firm*—Woodcock Washburn Kurtz Mackiewicz & Norris LLP

[57] ABSTRACT

Processes for preparing 2'-O-alkylated guanosine, uridine, cytidine, and 2,6-diaminopurine 3'-O-phosphoramidites include the steps of alkylating nucleoside precursors, adding suitable blocking groups and phosphitylating. For the guanosine 2'-O-alkylated 3'-O-phosphoramidites, alkylation is effected on 2,6-diamino-9-(β-D-ribofuranosyl)purine followed by deamination. For uridine 2'-O-alkylated 3'-O-phosphoramidites, alkylation is effect on a dialkyl stannylene derivative of uridine. For cytidine 2'-O-alkylated 3'-O-phosphoramidites, alkylation is effected directly on cytidine. Alkylation is effected directly upon 2,6-diaminopurine.

7 Claims, No Drawings

OTHER PUBLICATIONS

Kielanowska, M. et al., "Preparation and proterties of 2'-O-ethylcytidylic acid", *Nucl. Acids Res.,* 1976, 3(3), 817–824.

Kusmierek, J.T. et al., "Alkylation of Cytidine–5'–Phosphate: Mechanisms of Alkylation, Influence of O'–Alkylation on Suceptibility of Pyrimidien Nucleotides to Some Nucleolytic Enzymes, and Synthesis of 2'-O-Alkyl Polynucleotides", *Acta Biochimica Polonica,* 1973, 20(4), 365–381.

Pike, L.M. et al., "Mixed Alkylation (Methylation and Ethylation) of Adenosine by Diazoethane in Aqueous 1,2–Dimethoxyethane", *J. Org. Chem.,* 1974, 39(25), 3674–3676.

Ransford, G.H. et al., "2'–O–Ethyl Pyrimidine Nucleosides (1)", *J. Carbohydrates, Nucleosides, Nucleotides,* 1974, 1(3), 275–278.

Rottman, F. et al., "Influence of 2'–O–Alkylation on the Structure of Single–Stranded Polynucleotides and the Stability of 2'–O–Alkylated Polynucleotide Complexes", *Biochemistry,* 1974, 13, 2762–2771.

Tazawa, J.L. et al., "A Novel Procedure for the Synthesis of 2'–O–Alkyl Nucleotides", *Biochemistry,* 1972, 11, 4931–4937.

PROCESS FOR THE PREPARATION OF 2'-O-ALKYL PURINE PHOSPHORAMIDITES

CROSS REFERENCE TO RELATED APPLICATION

This application is a divisional application of U.S. application Ser. No. 08/888,880, filed Jul. 7, 1997, now U.S. Pat. No. 5,856,466, issued Jan. 5, 1999, which is a divisional application of U.S. application Ser. No. 08/410,002, filed Mar. 23, 1995, now U.S. Pat. No. 5,646,265, issued Jul. 8, 1997, which is a file wrapper continuation application of 07/968,849, filed Oct. 30, 1992, now abandoned, which is a continuation-in-part of U.S. application Ser. No. 07/967,267, filed on Oct. 27, 1992, which is a continuation-in-part of U.S. application Ser. No. 07/918,362, filed on Jul. 23, 1992, now U.S. Pat. No. 5,506,351, and U.S. application Ser. No. 07/854,634, filed Jul. 1, 1992, now abandoned, which is the U.S. national phase application of application PCT/US91/00243, filed Jan. 11, 1991, and a continuation-in-part application of U.S. application Ser. Nos. 07/463,358, filed Jan. 11, 1990, now abandoned, and 07/566,977, filed Aug. 13, 1990, now abandoned.

FIELD OF INVENTION

This application is directed to processes for the preparation of 2'-O-alkyl guanosine, uridine and cytidine phosphoramidites.

BACKGROUND OF THE INVENTION

A number of oligonucleotide analogs have been made. One class of oligonucleotides that have been synthesized are the 2'-O-substituted oligonucleotides. Such oligonucleotides have certain unique and useful properties. In U.S. patent application Ser. No. 814,961, filed Dec. 24, 1991, entitled Gapped 2' Modified Phosphorothioate oligonucleotides, assigned to the same assignee as this application, the entire contents of which are herein incorporated by reference, 2' substituted nucleotides are introduced within an oligonucleotide to induce increased binding of the oligonucleotide to a complementary target strand while allowing expression of RNase H activity to destroy the targeted strand.

In a recent article, Sproat, B. S., Beijer, B. and Iribarren, A., *Nucleic Acids Research*, 1990, 18:41, the authors noted further use of 2'-O-methyl substituted oligonucleotides as "valuable antisense probes for studying pre-mRNA splicing and the structure of spliceosomes".

2'-O-Methyl and ethyl nucleotides have been reported by a number of authors. Robins, et al., *J. Org. Chem.*, 1974, 39, 1891; Cotten, et al., *Nucleic Acids Research*, 1991, 19, 2629; Singer, et al., *Biochemistry* 1976, 15, 5052; Robins, Can. *J. Chem.* 1981, 59, 3360; Inoue, et al., *Nucleic Acids Research*, 1987, 15, 6131; and Wagner, et al., *Nucleic Acids Research*, 1991, 19, 5965;112.

Sproat, B. S. and Lamond, A. I., in "12'-O-Methyloligoribonucleotides: synthesis and applications, *Oligonucleotides and Analogs A Practical Approach*; Eckstein, F. Ed.; IRL Press, Oxford, 1991, describe syntheses of 2'-O-methylribonucleoside-3'-O-phosphoramidites. The uridine phosphoramidite synthesis described therein requires both base and sugar protection of the starting nucleoside prior to alkylation. Only after the base and sugar protecting groups are in place on the uridine is it then alkylated. Post alkylation, the base protecting group is removed followed by 5'-O-dimethoxytritylation and phosphitylation. The cytidine phosphoramidite synthesis described by Sproat and Lamond utilizes (and thus requires) the base and sugar blocked 2'-O-methyl uridine analog. This analog is then converted to a blocked cytidine analog, the blocking group is removed from the sugar, the analog is dimethoxytritylated and finally phosphitylated. The guanosine phosphoramidite synthesis taught by Sproat and Lamond starts from a 2-amino-6-chloronucleoside having 3' and 5' sugar hydroxy groups blocked. This nucleoside is converted to a 2,6-dichloro derivative. The dichloro compound is then 2'-O-alkylated. Following O-alkylation, the dichloro compound is converted to a diazido intermediate. The diazido intermediate is in turn converted to a diamino intermediate. The diamino intermediate is then deaminated to the guanosine analogue. The 2-amino group of the guanosine analogue is blocked followed by dimethoxytritylation and finally phosphitylation. This guanosine procedure is also published in Sproat, et. al., *Nucleic Acids Research*, 1991 19:733.

The above synthetic procedures involve multiple steps and numerous reagent treatments—9 different reagent treatments for uridine, 10 for cytidine and 12 for guanosine. For the cytidine and guanosine compounds at least one of the reagents that is required is not readily available and thus is a very expensive reagent.

Certain oligonucleotides containing 2'-O-alkyl substituted nucleotides are promising candidates for use as human pharmaceuticals. For use in large scale therapeutic testing and eventually for human pharmaceutical use, large amounts of these oligonucleotides must be synthesized. The large amounts of oligonucleotides in turn requires large amounts of the 2'-O-alkyl nucleoside phosphoramidites used in synthesizing the oligonucleotides. Consideration must therefore be given to both cost and purity of the starting phosphoramidites used in the synthesis of such oligonucleotides. As a general premise, as the number of synthetic steps increases, the cost of manufacture increases. Further as the number of steps increases, quality control problems escalate. In view of this, it is evident that there is a great need for new and improved procedures for preparing nucleoside phosphoramidites.

OBJECTS OF THE INVENTION

It is an object of this invention to provide new and improved synthetic methods for the preparation of 2'-substituted nucleoside phosphoramidites.

It is a further object of this invention to provide new and improved synthetic methods for the preparation of 2'-O-alkyl nucleoside phosphoramidites.

A further object of this invention is to provide new and improved syntheses of 2'-O-alkyl guanosine phosphoramidites.

A further object of this invention is to provide new and improved syntheses of 2'-O-alkyl cytidine phosphoramidites.

A further object of this invention is to provide new and improved syntheses of 2'-O-alkyl uridine phosphoramidites.

A further object of this invention is to provide new and improved syntheses of 2,6-diamino-9-(2'-O-alkyl-β-D-ribofuranosyl)purine phosphoramidites.

A further object of this invention is to provide new and improved oligonucleotide syntheses that utilize the improved phosphoramidite syntheses of the invention.

These and other objects will become apparent to persons of ordinary skill in the art from a review of the present specification and appended claims.

SUMMARY OF THE INVENTION

Previous methods for the preparation of 2-O-alkylated nucleoside phosphoramidites involved numerous steps and reagents, resulting in decreased efficiency and increased cost.

In accordance with this invention there are provided improved processes for the preparation of 2'-O-alkylated nucleoside phosphoramidites including 2'-O-alkylated guanosine, cytidine and uridine phosphoramidites. Further in accordance with this invention there are provided processes for the preparation of oligonucleotides that include at least one 2'-O-alkylated nucleotide incorporated within the oligonucleotide.

In accordance with the invention there are provided processes for preparing a 2'-O-alkylated guanosine 3'-O-phosphoramidite comprising the steps of alkylating a 2,6-di-amino-9-(ribofuranosyl)purine to form a 2,6-diamino-9-(2'-O-alkylated ribofuranosyl)purine; deaminating said 2,6-diamino-9-(2'-O-alkylated ribofuranosyl)purine to form a 21-O-alkylated guanosine; blocking the 5'-hydroxyl moiety of said 2'-O-alkylated guanosine; and phosphitylating the 3'-position of said 5'-blocked 2'-O-alkylated guanosine.

Further in accordance with the invention there are provided processes for preparing a 2'-O-alkylated cytidine 3'-O-phosphoramidite that include the steps of alkylating an unblocked cytidine to form a 2'-O-alkylated cytidine; blocking the 5'-hydroxyl moiety of said 2'-O-alkylated cytidine; and phosphitylating the 3'-position of said 5'-blocked 2'-O-alkylated cytidine.

Further in accordance with the invention there are provided processes for preparing a 2'-O-alkylated uridine 3'-O-phosphoramidite that include the steps of treating a uridine with a dialkyltin oxide to form a 2',3'-O-dialkylstannylene derivative of uridine; alkylating said stannylene derivative of uridine to form a 2'-O-alkylated uridine; blocking the 5'-hydroxyl moiety of said 2'-O-alkylated uridine; and phosphitylating the 3'-position of said 5'-blocked 2'-O-alkylated uridine.

Further in accordance with the invention there are provided processes for preparing a 2'-O-alkylated 2,6-diamino-9-(β-D-ribofuranosyl)purine 3'-O-phosphoramidite that include the steps of alkylating a 2,6-diamino-9-(β-D-ribofuranosyl)purine to provide a 2'-O-alkylated 2,6-diamino-9-(β-D-ribofuranosyl)purine; blocking the 5'-hydroxyl moiety of said 2'-O-alkylated 2,6-diamino-9-(β-D-ribofuranosyl)purine; and phosphitylating the 3'-position of said 5'-blocked 2'-O-alkylated 2,6-diamino-9-(β-D-ribofuranosyl)purine.

Further in accordance with the invention there are provided processes for preparing an oligonucleotide that include at least one 2'-O-alkylated guanosine nucleotide within the oligonucleotide, the processes comprise the steps of alkylating a 2,6-diamino-9-(ribofuranosyl)purine to form a 2,6-diamino-9-(2'-O-alkylated ribofuranosyl)purine; deaminating said 2,6-diamino-9-(2'-O-alkylated ribofuranosyl)purine to form a 2'-O-alkylated guanosine; blocking the 5'-hydroxyl moiety of said 2'-O-alkylated guanosine; phosphitylating the 3'-position of said 5'-blocked 2'-O-alkylated guanosine to form a 2'-O-alkylated guanosine 3'-O-phosphoramidite; and coupling, utilizing phosphoramidite coupling conditions, said 2'-O-alkylated guanosine 3'-O-phosphoramidite to a 5'-hydroxyl moiety of an oligonucleotide.

Further in accordance with the invention there are provided processes for preparing an oligonucleotide that include at least one 2'-O-alkylated cytidine nucleotide within the sequence of the oligonucleotide, the processes comprise the steps of alkylating a cytidine to provide a 2'-O-alkylated cytidine; blocking the 5'-hydroxyl moiety of said 2'-O-alkylated cytidine; phosphitylating the 3'-position of said 5'-blocked 2'-O-alkylated cytidine to form a 2'-O-alkylated cytidine 3'-O-phosphoramidite; and coupling, utilizing phosphoramidite coupling chemistry, said 2'-O-alkylated cytidine 3'1-O-phosphoramidite to a 5'-hydroxyl moiety of an oligonucleotide.

Further in accordance with the invention there are provided processes for preparing an oligonucleotide that include at least one 2'-O-alkylated uridine nucleotide within the sequence of the oligonucleotide, the processes comprise the steps of treating uridine with a dialkyltin oxide to form a 2',3'-O-dialkylstannylene derivative of uridine; alkylating said stannylene derivative to provide a 2'-O-alkylated uridine; blocking the 5'-hydroxyl moiety of said 2'-O-alkylated uridine; phosphitylating the 3'-position of said 5'-blocked 2'-O-alkylated uridine to form a 2'-O-alkylated uridine 3'-O-phosphoramidite; and coupling, utilizing phosphoramidite chemistry, said 2'-O-alkylated uridine 3'-O-phosphoramidite to a 5'-hydroxyl moiety of an oligonucleotide.

Further in accordance with the invention there are provided processes for preparing an oligonucleotide that include at least one 2'-O-alkylated 2,6-diamino-9-(β-D-ribofuranosyl)purine nucleotide within the sequence of the oligonucleotide, the processes comprise the steps of alkylating a 2,6-diamino-9-(β-D-ribofuranosyl)purine to provide a 2'-O-alkylated 2,6-diamino-9-(β-D-ribofuranosyl)purine; blocking the 5'-hydroxyl moiety of said 2'-O-alkylated 2,6-diamino-9-(β-D-ribofuranosyl)purine; phosphitylating the 3'-position of said 5'-blocked 2'-O-alkylated 2,6-diamino-9-(β-D-ribofuranosyl)purine to form a 2'-O-alkylated 2,6-diamino-9-(β-D-ribofuranosyl)purine 3'-O-phosphoramidite; and coupling, utilizing phosphoramidite chemistry, said 2'-O-alkylated 2,6-diamino-9-(β-D-ribofuranosyl)purine 3'-O-phosphoramidite to a 5'-hydroxyl moiety of an oligonucleotide.

In the context of this invention, the term "nucleoside" refers to a sugar and a base that are joined together, normally about an "anomeric" carbon on the sugar. Both α and β sugars are encompassed by the present invention. In preferred embodiments of the present invention the nucleoside sugar is a pentofuranosyl sugar, however, other sugars might also be utilized such as carbocyclic or 4'-deoxy-4'-thio sugar analogs.

The term "oligonucleotide" refers to polynucleotides formed from a plurality of nucleoside units that are joined by phosphorous linkages. These phosphorous linkages included phosphodiester linkages, phosphorothioate linkages, phosphotriester linkages and alkylphosphonates, all of which can be synthesized via phosphoramidite coupling chemistry, and phosphorodithioate linkages, which can be synthesized via phosphorothioamidite coupling chemistry. Other modifications consistent with the spirit of this invention are also deemed to be within the scope of the invention.

Further as used in this invention, the term "alkylating" refers to the addition of an alkyl, alkenyl or alkynyl moiety, preferably an alkyl moiety, to the precursors of the nucleosides phosphoramidites of the invention. Alkylation of the 2' position of the nucleoside sugar links the alkylating moiety to the 2' position of the sugar via an ether linkage.

Preferred alkyl moieties include un-substituted and substituted straight chain $C_1$–$C_{20}$, alkyl and un-substituted and substituted branch chain $C_1$–$C_{20}$ alkyl. Preferred alkenyl groups include un-substituted and substituted straight chain $C_2$–$C_{20}$ alkenyl, and un-substituted and substituted branch chain $C_2$–$C_{20}$ alkenyl. Preferred alkynyl groups include un-substituted and substituted straight chain $C_2$–$C_{20}$ alkynyl and un-substituted and substituted branch chain $C_2$–$C_{20}$ alkynyl. Thus preferred alkylation groups include but are not limited to $C_1$ to $C_{20}$ straight or branched chain lower alkyl or substituted lower alkyl, $C_2$ to $C_{20}$ straight or branched chain lower alkenyl or substituted lower alkynyl, $C_2$ to $C_{20}$ straight or branched chain lower alkynyl or substituted lower alkynyl.

Alkyl groups of the invention include but are not limited to $C_1$–$C_{20}$ straight and branched chained alkyls such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl, isopropyl, 2-butyl, isobutyl, 2-methylbutyl, isopentyl, 2-methyl-pentyl, 3-methylpentyl, 2-ethylhexyl and 2-propyl-pentyl. Alkenyl groups include, but are not limited to, unsaturated moieties derived from the above alkyl groups including, but not limited to, vinyl, allyl and crotyl. Alkynyl groups include unsaturated moieties having at least one triple bond that are derived from the above alkyl groups including, but not limited to, ethynyl and propargyl.

Substituent groups for the above include, but are not limited to, alkyl groups, alkenyl groups, and alkynyl groups such as alicyclic alkyl, alicyclic alkenyl, alicyclic alkynyl, haloalkyl, haloalkenyl, haloalkynyl, alkoxy, thioalkoxy, haloalkoxy, carbocyclic, heterocyclic and aryl groups as well as halogen, hydroxyl, amino, azido, carboxy, cyano, nitro, mercapto, sulfide, sulfone and sulfoxide groups. Other suitable substituent groups include steroids, reporter groups, reporter enzymes, lipophilic molecules, peptides, protein, vitamins, RNA cleaving complexes, metal chelators, alkylators, intercalators, cross-linking agents, rhodamines, coumarins, acridones, pyrenes, stilbenes, oxazolo-pyridocarbazoles, anthraquinones, phenanthridines, phenazines, azidobenzenes, psoralens, porphyrins, cholic acids, folic acids and cholesterols. Aryl groups include but are not limited to phenyl, tolyl, benzyl, naphthyl, anthracyl, phenanthryl, pyrenyl, and xylyl. Halogens include fluorine, chlorine and bromine. Suitable heterocyclic groups include but are not limited to imidazole, tetrazole, triazole, pyrrolidine, piperidine, piperazine and morpholine. Amines include amines of all of the above alkyl, alkenyl, alkynyl and aryl groups including primary and secondary amines and "masked amines" such as phthalimide. Amines are also meant to include polyalkylamino compounds and aminoalkylamines such as aminopropylamine and further heterocyclo-alkylamines such as imidazol-1,2 or 4-yl-propylamine. RNA cleaving complexes may be, for example, intercalators or groups which bind in the minor groove of RNA. Intercalators are molecules which insert themselves between neighboring bases of an olignoucleotide. A well known intercalator is acridine. Reporter molecules are molecules which may aid in the identification of a molecule, either visually or otherwise. For example, biotin and various fluorophores are effective reporter groups. Cross-linking agents effectively join two groups. Some cross-linking agents are commercially available such as biotin or 3'-maleimidobenzoyl-N-hydroxy-succinimide available from Boeringer Mannheim (Indianapolis, Ind.).

In accordance with methods of the present invention, the alkylation is preferably conducted in the presence of a base, preferably a metal hydride such as sodium hydride. Alkylation of the 2',3'-O-dialkylstannylene derivative of uridine preferably is performed in the presence of a salt such as a metal halide. Cesium flouride and sodium iodide are preferred in some embodiments of the present invention. Additionally, the 5' hydroxyl blocking group is preferably a dimethoxytrityl moiety. The phosphitylating reagent is preferably bis-N,N-diisopropylaminocyanoethylphosphite and the phosphitylating reaction is preferably conducted in the presence of N,N-diisopropylamino-hydrotetrazolide.

In effecting the alkylation of uridine, 2',3'-O-(dibutylstannylene)uridine is alkylated. The dibutylstannylene derivative in turn was prepared in one step from uridine by reaction with dibutyl tin oxide utilizing the procedure of by Wagner, D., Verheyden, J. P. H. and Moffat, J. G., *J. Org. Chem.* 1974, 39:24. As noted by these authors, 2',3'-di-O-(dibutylstannylene)nucleosides are activated towards alkylation. By using the dibutylstannylene derivative alkylation of the sugar hydroxyls was effected without concurrent alkylation of the uracil base. The dibutylstannylene group thus served as a activating group not a blocking group.

For the synthesis of N4-benzoyl-5'-O-(4,4'-dimethoxytriphenylmethyl)-2'-O-methyl cytidine 3'-O-β-cyanoethyl-N,N-diisopropylaminophosphoramidite two methods for the preparation of the intermediate N4-benzoyl-2'-O-methylcytidine are compared. Method A involves blocking of the 3'–5' sites with the TIPS-Cl reagent to allow methylation only on the 2' position. Method B, a preferred method of the invention, uses a direct methylation of cytidine followed by separation of the resulting mixture of 2' and 3' isomers. The overall yields are comparable. In using Method B, the 2'-O-isomer can be crystallized out from the mixture, filtered and the remaining mother liquors taken through the dimethoxytritylation step prior to separation of the 2' and 3' isomers or alternately the totality of the alkylated cytidine. can be taken through the dimethoxytritylation step with separation of the 2' isomer only effected after this step.

In effecting the alkylation of guanosine, 2',6 diaminopurine is alkylated, for example, by methods described in U.S. patent application Ser. No. 07/967,267, filed Oct. 27, 1992.

The amino moiety of the phosphoramidites of the invention can be selected from various amines presently used for such phosphoramidites. Such amines include both aliphatic and heteroaryl amines as are described in various United States patents, principally those to M. Caruthers and associates.

These include U.S. Pat. No. 4,668,777, issued May 26, 1987; U.S. Pat. No. 4,458,066, issued Jul. 3, 1984; U.S. Pat. No. 4,415,732, issued Nov. 15, 1983; and U.S. Pat. No. 4,500,707, issued Feb. 19, 1985, all of which are herein incorporated by reference. One preferred amino group is diisopropylamino.

In addition to the amino moiety of the phosphoramidite, for phosphodiester and phosphorothioate linkages, an additional phosphorous blocking group is used. One preferred blocking group is the cyanoethyl group. Other phosphorous blocking groups include methoxy and 2-(methylsulphonyl) ethyl. Additionally an activating agent is normally used for the phosphoramidite coupling chemistry. One preferred activating agent is N,N-diisopropylaminohydro-tetrazolide. Other suitable moieties for these functions are also disclosed in the above noted patents as well as in U.S. Pat. No. 4,725,677, issued Feb. 16, 1988 and Berner, S., Muhlegger, K., and Seliger, H., *Nucleic Acids Research* 1989, 17:853; Dahl, B. H., Nielsen, J. and Dahl, O., *Nucleic Acids Research* 1987, 15:1729; and Nielson, J. Marugg, J. E., Van Boom, J. H., Honnens, J., Taagaard, M. and Dahl, O., *J. Chem. Research* 1986, 26, all of which are-herein incorporated by reference.

For use in phosphorothioate linkage, the Beaucage reagent is described in Beaucage, S. L. and Caruthers, M. H., *Tetrahedron Letters* 1981, 22:1859 as well as in Zon, G. and Stec, J., Phosphorothioate oligonucleotides: *Oligonucleotides and Analogs A Practical Approach*; Eckstein, F. Ed.;

IRL Press, Oxford, 1991, which also describes sulfurization by elemental sulfur.

EXAMPLES

The following examples illustrate the invention, however, they are not intended as being limiting. In various examples the nomenclature 4,4'-dimethoxytriphenylmethyl and dimethoxytrityl are used interchangeably to reference the DMT blocking group positioned on the 5'-hydroxyl moiety of the various nucleoside and nucleotides of the invention.

NMR spectra were obtained with the following instruments: $^1$H-NMR: Varian Gemini-200 (199.975 MHz), $^{13}$C-NMR: Varian Gemini-200 (50.289 MHz). NMR spectra were recorded using either deuteriochloroform (tetramethylsilane as internal standard) or dimethylsulfoxide-$d_6$ as solvent. The following abbreviations were used to designate the multiplicity of individual signals: s=singlet, d=doublet, t=triplet, q=quartet, ABq=ab quartet, m=multiplet, dd=doublet of doublets, br s=broad singlet. Mass spectra were acquired on a VG 70-SEQ instrument (VG Analytical (Fisons)), using fast atom bombardment ionization (7 kV Xe atoms). Solvent ratios for column chromatography are given as volume/volume. Evaporations of solvents were performed in vacuo (60 torr) at 30° C. unless otherwise specified. Melting points are reported uncorrected.

Example 1

2,6-Diamino-9-(β-D-ribofuranosyl)purine

In accordance with modifications of the procedures described in Robins, M. J., Hanske, F. and Beriner, S. E., *Can. J. Chem.*, 59:3360 (1981), guanosine hydrate (49 g, Aldrich Chemical Co.), toluene (200 ml), hexamethyldisilazane (160 ml, 4.3 eq) and trifluoromethanesulfonic acid (3.7 ml) were loaded, in a stainless steel Parr bomb. The bomb was sealed and heated. approximately ⅓ submerged in an oil bath at 170° C .for 5 days. The bomb was cooled in a dry ice acetone bath and. opened. The contents were transferred to a 2 liter round. bottom flask using methanol (MeOH) and the solvent evaporated on a Buchii evaporator. 1:1 H$_2$O/MeOH (600 ml) was added to the residue and the resulting brown suspension was refluxed 4–5 hr. The resulting suspension was evaporated on the Buchii. evaporator to remove the methanol (≈½ volume). Additional H$_2$O (≈300 ml) was added and the mixture was heated, treated with charcoal and filtered through a Celite filter pad. Upon cooling, a crystalline solid formed. The solid was isolated by filtration, washed with H$_2$O and dried under high vacuum at 90° C. to yield the product (43.7 g, 89% yield) as a tan solid. UV and NMR spectra of this compound compared to literature values.

This variation of the procedures of Robins, et al. supra, eliminated the need to utilize liquid ammonia in the reaction mixture since the ammonia molecule is generated in situ from the silazane reagent and the water of hydration of the guanosine hydrate starting material. Further, the use of chlorotrimethylsilane was not necessary nor was it necessary to conduct the reaction under anhydrous conditions, do a preliminary evaporation, or open and re-seal the Parr bomb under a dry nitrogen atmosphere.

Example 2

2,6-Diamino-9-(2'-O-propyl-β-D-ribofuranosyl) purine & 2,6-Diamino-9-(3-O-propyl-β-D-ribofuranosyl)purine Sodium hydride (NaH) (2.1 g) was added to 2,6-diamino-9-(β-D-ribofuranosyl)purine (10.5 g) in dry dimethylformamide (DMF) (150 ml). After stirring for 10 min, iodopropane (6 ml) was added. The solution was stirred for 45 min at room temperature followed by the addition of a further aliquot of NaH (600 mg). The reaction mixture was stirred overnight and then quenched by the addition of ethanol (EtOH) (5 ml). The reaction mixture was evaporated in vacuo, the residue suspended in 10% MeOH/CH$_2$Cl$_2$ and purified by silica gel chromatography (300 g) using 5→10% MeOH/CH$_2$Cl$_2$ as the eluent. The 2',3'-di-O-propyl product eluted first followed by the 2'-O-propyl product and then the 3'-O-propyl product. The 2'-O-propyl product containing fractions were pooled and the solvent stripped to yield a crude foam. The foam was crystallized from H$_2$O (40 ml), washed with cold H$_2$O and dried to yield 2.9 g of the 2'-O-propyl compound. The mother liquor was evaporated, re-chromatographed and crystallized to yield an additional 2.4 g of the 2'-O-propyl compound. The second mother liquor was evaporated to yield 4 g of a mixture of 2' and 3'-O-propyl compounds as an oil. Fractions containing the 3'-O-propyl product as the major product were evaporated and residue crystallized from water. (See Example 17 below for isolation and characterization of the 2',3'-di-O-propyl compound).

2,6-Diamino-9-(2'-O-propyl-β-D-ribofuranosyl)purine $^1$H NMR (DMSO-$\underline{d}_6$) δ 0.76 (t, 3, C$\underline{H}_3$), 1.4 (tq, 2, C$\underline{H}_2$), 3.3 (m, 1, H-5"+HDO), 3.65–3.45 (m, 3, $\underline{H}$-5', O—C$\underline{H}_2$), 3.9 (m, 1), 4.25 (br m, 1), 4.38 (dd, 1), 5.1 (br d, 1 3'-O$\underline{H}$), 5.45 (br t, 1, 5'-OH), 5.75 (br s, 2, 6-N$\underline{H}_2$), 5.83 (d, 1, $\underline{H}$-1'), 6.77 (br s, 2, 2-N$\underline{H}_2$) and 7.95 (s, 1, $\underline{H}$-8). Anal. Calcd. for C$_{13}$H$_{20}$N$_6$O$_4$·½H$_2$O: C, 46.91; H, 6.2; N,25.25. Found: C, 47.09; H, 6.37; N, 25.33.

2,6-Diamino-9-(3'-O-propyl-β-D-ribofuranosyl)purine $^1$H NMR (DMSO-$\underline{d}_6$) δ 0.75 (t, 3, C$\underline{H}_3$), 1.4 (tq, 2, C$\underline{H}_2$), 3.27–3.5 (ABX 2, O—C$\underline{H}_2$—), 3.5 and 3.6 (ABX, 2, $\underline{H}$-5'), 3.9 (m,1), 4.22 (m, 1), 4.35 (m, 1), 5.1 (br d, 1, 2'-O$\underline{H}$), 5.45 (br t, 1, 5'-O$\underline{H}$), 5.75 (br s, 2, 6-N$\underline{H}_2$), 5.8 (d, 1, $\underline{H}$-1'), 6.8 (br s, 2C$\underline{H}_2$, 2-$\underline{H}_2$) and 7.95 (s, 1, $\underline{H}$-8).

Example 3

2'-O-Propylguanosine

A mixture of 2,6-Diamino-9-(2'-O-propyl-β-D-ribofuranosyl)purine and 2,6-Diamino-9-(3'-O-propyl-β-D-ribofuranosyl)purine (4.6 gm) and adenosine deaminase (200 mg, Sigma Chemicals Type II) were stirred at room temperature overnight in 0.1 M tris buffer (150 ml, pH 7.4), DMSO (100 ml) and 0.1 M sodium phosphate buffer (10 ml). A further aliquot of adenosine deaminase (140 mg) in 0.1 M phosphate buffer (30 ml) and DMSO (20 ml) was added and the reaction stirred an addition 24 hrs. The solvent was evaporated in vacuo and the residue flash chromatographed on silica gel utilizing 5→20% MeOH/CH$_2$Cl$_2$. Product-containing fractions were evaporated in vacuo and the residue crystallized from H$_2$O to yield 2.6 gm of product. m.p. dec>270° C. $^1$H NMR (DMSO-$\underline{d}_6$) δ 0.75 (t, 3, C$\underline{H}_3$), 1.42 (tq, 2, C$\underline{H}_2$), 3.3–3.6 (m, 4, $\underline{H}$-5', O—C$\underline{H}_2$), 3,85 (m, 1), 4.2 (m, 1), 4.23 (m, 1), 5.10 (t, 1, 5'-O$\underline{H}$), 5.13 (d, 1, 3'-O$\underline{H}$), 5.75 (d, 1, $\underline{H}$-1'), 6.45 (br s, 2, N$\underline{H}_2$), 7.95 (s, 1, $\underline{H}$-8) and 10.67 (br s, 1, N$\underline{H}$) . Anal. Calcd. for C$_{13}$H$_{19}$N$_5$O$_5$: C, 47.99; H, 5.89; N, 21.53. Found: C, 47.90, H, 5.85; N, 21.44.

Example 4

N2-Isobutyryl-2'-O-propylguanosine

2'-O-Propylguanosine (3.6 gm) in pyridine (50 ml) was; cooled in an ice bath and trimethylsilyl chloride (8.4 ml, 6 eq.) was added. The reaction mixture was stirred for 30 min and isobutyryl chloride (5.8 ml, 5 eq.) was added. The solution was stirred for 4 hours during which it was allowed to warm to room temperature. The solution was cooled, $H_2O$ added (10 ml) and the solution was stirred for an additional 30 mins. Concentrated $NH_4OH$ (10 ml) was added and the solution evaporated an vacuo. The residue was purified by silica gel chromatography using 10% $MeOH/CH_2Cl_2$ to elute the product. Product-containing fractions were evaporated to yield 2.5 g of product as a foam. An analytical sample was re-chromatographed on silica and eluted with $CH_2Cl_2 \rightarrow 6\%$ $MeOH/CH_2Cl_2$. $^1H$ NMR (DMSO-$d_6$) δ 0.75 (t, 3, C$\underline{H}_3$), 1.13 [d, 6, CH(C$\underline{H}_3$)$_2$], 1.4 (m, 2, C$\underline{H}_2$), 2.75 [m, 1, C$\underline{H}$(CH$_3$)$_2$], 3.52 (m, 6, OC$\underline{H}_2$), 3.36 and 3.6 (ABX, 2, $\underline{H}$-5'), 3.95 (m, 1), 4.26 (m, 1), 4.33 (m, 1), 5.07 (t, 1, 5'-O$\underline{H}$), 5.18 (d, 1, 3'-O$\underline{H}$), 5.9 (d, 1, H-1'), 8.25 (s, 1, $\underline{H}$-8), 11.65 (br s, 1, N$\underline{H}$) and 12.1 (br s, 1, NH). Anal. Calcd. for $C_{17}H_{25}N_5O_6 \cdot \frac{1}{2}H_2O$: C, 50.49; H, 6.48; N, 17.32. Found: C, 50.81; H, 6.62; N, 17.04.

Example 5

N2-Isobutyryl-5'-dimethoxytrityl-2'-O-propylguanosine

N2-Isobutyryl-2'-O-propylguanosine (2.64 g) was co-evaporated with pyridine and then solubilized in pyridine (180 ml). Dimethoxytrityl chloride (2.4 g, 1.1 eq) and dimethylaminopyridine (50 mg) were added with stirring at room temperature. The reaction mixture was stirred overnight and evaporated in vacuo. The residue was partitioned between $CH_2Cl_2/2 \times$dil $Na_2CO_3$. The organic phase was dried (MgSO$_4$) and evaporated. The residue was purified by silica gel chromatography (1:1 EtOAc/Hex→5% MeOH/EtOAc, 1% TEA) to yield 4.1 g of product. $^1H$ NMR (DMSO-$d_6$) δ 0.78 (t, 3, C$\underline{H}_3$), 1.12 [d, 6, CH(C$\underline{H}_3$)$_2$], 1.46 (m, 2, C$\underline{H}_2$), 2.75 [m, 1, C$\underline{H}$(CH$_3$)$_2$], 3.35 and 3.55 (ABX, 2, $\underline{H}$-5'), 3.73 (s, 6, OC$\underline{H}_2$), 4.0 (m, 1), 4.3 (m, 1), 4.4 (m, 1), 5.18 (d, 1, 3'-O$\underline{H}$), 5.93 (d, 1, $\underline{H}$-1'), 6.8, 7.2, 7.36 (m, 13, DMTr), 8.13 (s, 1, $\underline{H}$-8), 11.63 (br s, 1, N$\underline{H}$) and 12.1 (br s, 1, N$\underline{H}$). Anal. Calcd. for $C_{38}H_{42}N_5O_8 \cdot H_2O$: C, 63.83; H, 6.20; N, 9.80. Found: C, 64.22; H, 6.35; N, 9.55.

Example 6

N2-Isobutyryl-5'-dimethoxytrityl-2'-O-propylguanosine 3'-β-cyanoethyl-N,N-diisopropylphosphoramidite A $CH_2Cl_2$ solution of N2-Isobutyryl-5'-dimethoxytrityl-2'-O-propylguanosine (4.1 g), bis-(N,N-diisopropylamino)-2-cyanoethylphosphite (3.7 ml, 2 eq) and N,N-diisopropylammonium tetrazolide (0.5 g, 0.5 eq) was stirred at room temperature overnight. The solution was partitioned against dil. $Na_2CO_3$ and then dil. $Na_2CO_3$/NaCl and dried over NgSO$_4$. The solvent want evaporated in vacuo and the residue was purified by silica gel chromatography (120 g, 1% TEA in EtOAc) to yield 5.2 g of product as a foam. $^{31}P$ NMR (CDCl$_3$) δ 150.5, 150.8.

Example 7

2,6-Diamino-9-(2'-O-pentyl-β-D-ribofuranosyl) purine & 2,6-Diamino-9-(3'-O-pentyl-β-D-ribofuranosyl)purine 2,6-Diamino-9-(β-D-ribofuranosyl)purine (10 g) was treated with sodium hydride (1.7 g, 1.2 eq) and bromopentane (5.3 ml, 1.2 eq) in DMF (90 ml) as per the procedure of Example 2. Silica gel chromatography yielded three components. The first eluted component (not characterized but believed to be the 2,3-di-(O-pentyl) compound was isolated as an oil (700 mg). The next component isolated as a foam (3.3 g) was crystallized from MeOH to yield 2.8 g of 2,6-diamino-9-(2'-O-pentyl-β-D-ribofuranosyl)purine. The third component isolated as a solid (200 mg) was crystallized from MeOH to yield 80 mg of 2,6-diamino-9-(3-O-pentyl-β-D-ribofuranosyl)purine. Fractions containing mixtures of the first and second components were evaporated and the residue crystallized from MeOH to yield at further 900 mg of the 2-O-pentyl compound. Further fraction yielded 1.2 g of a mixture of the 2'-O-pentyl and 3'-O-pentyl compounds.

2,6-Diamino-9-(2'-O-pentyl-β-D-ribofuranosyl)purine $^1H$ NMR (DMSO-$d_6$) δ 0.75 (t, 3, C$\underline{H}_3$), 1.16 (m, 4, C$\underline{H}_2$), 1.39 (m, 2, C$\underline{H}_2$), 3.53 (m, 2, C$\underline{H}_2$), 3.3 and 3.6 (ABX, 2, $\underline{H}$-5'), 3.93 (br s, 1), 4.23 (m, 1), 4.38 (m, 1), 5.1 (d, 1 3'-O$\underline{H}$), 5.5 (t, 1, 5'-OH), 5.75 (br s, 2, 6-NH$_2$), 5.82 (d, 1, $\underline{H}$-1'), 6.8 (br s, 2, 2-N$\underline{H}_2$) and 7.93 (s, 1, $\underline{H}$-8).

2,6-Diamino-9-(3'-O-pentyl-β-D-ribofuranosyl)purine $^1H$ NMR (DMSO-$d_6$) δ 0.87 (t, 3, C$\underline{H}_3$), 1.3 (m, 4, C$\underline{H}_2$), 1.55 (m, 2, C$\underline{H}_2$), 3.5 (m, 2, O—C$\underline{H}_2$—), 3.6 (m, 2, $\underline{H}$-5'), 3.86 (m, 1), 3.95 (m, 1), 4.6 (m, 1), 5.32 (br d, 1 2'-O$\underline{H}$), 5.46 (br t, 1, 5'-OH), 5.70 (d, 1, $\underline{H}$-1'), 5.75 (br s, 2, 6-N$\underline{H}_2$), 6.76 (br s, 2, 2-N$\underline{H}_2$) and 7.93 (s, 1, $\underline{H}$-8).

Example 8

2'-O-Pentylguanosine 2,6-diamino-9-(2'-O-pentyl-δ-D-ribofuranosyl)purine (1.9 g) in 0.1 M sodium phosphate buffer (50 ml, pH 6.0) and DMSO (25 ml) was treated with adenosine deaminase (added in two aliquots—first aliquot 50 mg, second aliquot 80 mg) at 35° C. as per the procedure of Example 3 to yield 1.4 g of product. $^1H$ NMR (DMSO-$d_6$) δ 0.8 (t, 3, C$\underline{H}_3$), 1.16 (m, 4, 2× CH$_2$), 1.4 (m, 2, CH$_2$), 3.38, 3.6 (m, 4, OC$\underline{H}_2$, $\underline{H}$-5'), 3.93 (s, 1, $\underline{H}$-4'), 4.28 (m, 2, $\underline{H}$-2', $\underline{H}$-3'), 5.17 (br, 2, 5', 3'-O$\underline{H}$), 5.8 (d, 1, $\underline{H}$-1'), 6.53 (br s, 2, N$\underline{H}_2$), 8.0 (s, 1, $\underline{H}$-8) and 10.68 (br, 1, N$\underline{H}$).

Example 9

N2-Isobutyryl-2'-O-pentylguanosine

2'-O-pentylguanosine (2.3 g) in pyridine (35 ml) was treated with trimethylsilyl chloride (4.15 ml, 5 eq) and isobutyryl chloride (3.4 ml, 5 eq) as per the procedure of Example 4 to yield the product as a foam (2.3 g). An analytical sample was crystallized from EtOAc/Hex. m.p. 178–180° C. $^1H$ NMR (DMSO-$d_6$) δ 0.75 (t, 3, C$\underline{H}_3$), 1.1 [m, 10, 2×C$\underline{H}_2$, CH(C$\underline{H}_3$)$_2$], 1.4 (m, 2, C$\underline{H}_2$), 2.74 [m, 1, C$\underline{H}$(CH$_3$)$_2$], 3.56 (m, 4, OC$\underline{H}_2$, $\underline{H}$-5'), 3.93 (m, 1, $\underline{H}$-4'), 4.25 (m, 1), 4.34 (m, 1), 5.0 (t, 1, 5'-O$\underline{H}$), 5.17 (d, 1, 3'-O$\underline{H}$), 5.88 (d, 1, $\underline{H}$-1'), 8.27 (s, 1, $\underline{H}$-8), 11.65 (br s, 1, N$\underline{H}$) and 12.05 (br s, 1, N$\underline{H}$). Anal. Calcd. for $C_{19}H_{29}N_5O_6$: C, 53.89; H, 6.90; N, 16.54. Found: 53.75; H, 6.92; N, 16.40

Example 10

N2-Isobutyryl-5'-dimethoxytrityl-2'-O-pentylguanosine

N2-Isobutyryl-2'-O-pentylguanosine (2.3 g) was treated with dimethoxytrityl chloride (1.7 g, 1.1 eq), and dimethylaminopyridine (100 mg as a catalyst) in pyridine (50 ml) as per the procedure of Example 5 to yield the product as a foam (2.9 g). $^1H$ NMR (DMSO-$d_6$) δ 0.83 (t, 3, C$\underline{H}_3$), 1.2 [m, 10, 2× C$\underline{H}_2$, CH(C$\underline{H}_3$)$_2$], 1.48 (m, 2, C$\underline{H}_2$), 2.78 [m, 1, CH(CH$_3$)$_2$], 3.4, 3.6 (m, 4, OCH$_2$, H-5'), 3.75 (s, 6, OCH$_3$), 4.07 (m, 1), 4.27 (m, 1), 4.42 (m, 1), 5.2 (br d, 1, 3'-OH), 5.95 (d, 1, H-1'), 6.85, 7.25, 7.38 (m, 13, DMTr), 8.15 (s, 1, H-8), 11.67 (br s, 1, NH) and 12.1 (br s, 1, NH). Anal. Calcd. for Anal. Calcd. for C$_{40}$H$_{47}$N$_5$O$_8$·½H$_2$O: C, 65.38; H, 6.58; N, 9.53. Found: C, 65.37; H, 6.59; N, 9.39.

Example 11

N2-Isobutyryl-5'-dimethoxytrityl-2'-O-pentylguanosine 3'-β-cyanoethyl-N,N-diisopropylphosphoramidite

N2-Isobutyryl-5'-dimethoxytrityl-2'-O-pentyl-guanosine (1.7 g) was treated with bis-(N,N-diisopropylamino)-2-cyanoethyl-phosphite (1.48 g) and N,N-diisopropylammonium tetrazolide (200 mg) as per the procedure of Example 6 to yield the product (1.4 g). $^{31}$P NMR (CDCl$_3$) δ 150.5, 150.85.

Example 12

2,6-Diamino-9-(2'-O-nonyl-β-D-ribofuranosyl)purine

2,6-Diamino-9-(β-D-ribofuranosyl)purine (50 g, 180 mmol) was treated with sodium hydride (8.8 g, 220 mmol) and bromononane (59 g, 54.4 ml, 285 mmol) in DMF (700 ml) as per the procedure of Example 2 (the diamino compound in DMF was cooled in an ice bath during the addition of NaH) to yield 83 g of crude product. 50 g of crude product was purified by silica gel chromatography. Fraction containing 2'-O-nonyl and 3'-O-nonyl product were combined to give a 77:23 mixture (29 g) of the 2' and 3' product. Pure 2'-O-nonyl product is obtained by chromatography. $^1$H NMR (DMSO-d$_6$) δ 0.95 (t, 3, CH$_3$); 1.17 [m, 12, O—CH$_2$—CH$_2$—(CH$_2$)$_6$]; 1.42 [m, 2, O—CH$_2$C H$_2$(CH$_2$)$_6$]; 3.27–3.70 (m, 2, H-5'); 3.50–3.70 [m, 2, O—C H$_2$(CH$_2$)$_7$]; 3.95 (m, 1, H-4'), 4.24 (m, 1, H-3'); 4.40 (m, 1, H-2'); 5.10 (d, 1, 3'-OH, J=5 Hz); 5.50 (t, 1, 5'-OH, J=6 Hz); 5.76 (s, 2, 2-NH$_2$); 5.83 (d, 1, H-1', J=6.0 Hz); 6.81 (s, 2, 6-N H$_2$); and 7.96 (s, 1, 8-H).

Example 13

2'-O-Nonylguanosine

A mixture of 2,6-diamino-9-(2'-O-nonyl-β-D-ribofuranosyl)purine and 2,6-diamino-9-(3'-O-nonyl-β-D-ribofuranosyl)purine (≈80:20 mixture, 29 g) in 0.1 M sodium phosphate buffer (50 ml, pH 7.4), 0.1 M tris buffer (1800 ml, pH 7.4) and DMSO (1080 ml) was treated with adenosine deaminase (1.6 g) as per the procedure of Example 3 to yield 60 g of product as an oil. An analytical product was purified by silica gel chromatography and recrystallized from EtOAc. m.p. 258–259° C. $^1$H NMR (DMSO-d$_6$) δ 0.96 (t, 3, CH$_3$, J=7 Hz); 1.17 [m, 12, O—CH$_2$—CH$_2$—(CH$_2$)$_6$]; 1.42 [m, 2, O—CH$_2$C H$_2$(CH$_2$)$_6$]; 3.27–3.61 (m, 4, H-5', O—CH$_2$(CH$_2$)$_7$]; 3.95 (m, 1, H-4'), 4.10–4.13 (m, 2, H-2', H-3'); 5.13–6.06 (m, 2, 3'-OH 5'-OH); 5.80 (d, 1, H-1', J=6.4 Hz); 6.47 (s, 2, 2-NH$_2$); 7.98 (s, 1, 8-H) and 10.64 (s, 1, N$_1$ amide). Anal. Calcd. for C$_{19}$H$_{31}$N$_5$O$_5$: C, 55.73; H, 7.63; N, 17.10. Found: C, 55.67; H, 7.66; N, 17.02.

Example 14

N2-Isobutyryl-2'-O-nonylguanosine

2'-O-nonylguanosine (14.7 g) in pyridine (360 ml) was treated with trimethylsilyl chloride (23.4 ml) and isobutyryl chloride (30.6 ml) as per the procedure of Example 4 to yield crude product (37 g). The crude material was purified by silica gel chromatography (eluted with 90/10 CHCl$_3$/MeOH) to yield 14.6 g of product re-crystallized from EtOAc. m.p. 168–169° C. $^1$H NMR (DMSO-d$_6$) δ 0.85 [t, 3, CH$_3$(nonyl)], 1.14 [m, 18, O—CH$_2$CH$_2$(CH$_2$)$_6$, CH(CH$_3$)$_2$], 1.40 [m, 2, O—CH$_2$CH$_2$(CH$_2$)$_6$], 2.79 [m, 1, CH(CH$_3$)$_2$], 3.31–3.63 (m, 4, H-5', O—CH$_2$(CH$_2$)$_7$; 3.96 (m, 1, H-4'), 4.27–4.37 (m, 2, H-2', H-3'); 5.10 (t, 1, 5'-OH, J=5 Hz), 5.18 (d, 1, 3'-OH, J=4 Hz), 5.91 (d, 1, H-1', J=6.6 Hz), 8.31 (s, 1, 8-H), 11.73 (s, 1, C$_2$ amide) and 12. 11 (s, 1, N$_1$ amide). Anal. Calcd. for C$_{23}$H$_{37}$N$_5$O$_6$: C, 57.60; H, 7.78; N, 14.60. Found: C, 57.63; H, 7.92; N, 14.62.

Example 15

N2-Isobutyryl-5'-dimethoxytrityl-2'-O-nonylguanosine

N2-Isobutyryl-2'-O-nonylguanosine (14.6 g, 30.4 mmol) was treated with dimethoxytrityl chloride (12.1 g, 34 mmol) in pyridine (200 ml) as per the procedure of Example 5 to yield 16 g of purple foam prior to chromatography and 11.5 g after chromatography purification. $^1$H NMR (DMSO-d$_6$) δ 0.84 [t, 3, CH$_3$(nonyl), J=7 Hz), 1.16 [m, 18, O—CH$_2$CH$_2$(C H$_2$)$_6$, CH(CH$_3$)$_2$], 1.43 [m, 2, O—CH$_2$CH$_2$(CH$_2$)$_6$], 2.77 [m, 1, CH(CH$_3$)$_2$], 3.18–3.63 (m, 4, H-5', O—CH$_2$(CH$_2$)$_7$]; 3.74 (s, 6, DMTr O—CH$_3$) 4.06 (m, 1, H-4'), 4.27 (m, 1, H-3'); 4.42 (m, 1, H-2'); 5.19 (d, 1, 3'-OH, J=5 Hz), 5.94 (d, 1, H-1', J=5.7 Hz), 6.83–7.38 (m, 13, DMTr aromatic), 8.14 (s, 1, 8-H), 11.65 (s, 1, C$_2$ amide) and 12.11 (s, 1, N$_1$ amide). Anal. Calcd. for C$_{44}$H$_{55}$N$_5$O$_8$: C, 67.59; H, 7.27; N, 8.96. Found: C, 67.59; H, 7.11; N, 8.80.

Example 16

N2-Isobutyryl-5'-dimethoxytrityl-2'-O-nonylguanosine 3'-β-cyanoethyl-N,N-diisopropylphosphoramidite

N2-Isobutyryl-5'-dimethoxytrityl-2'-O-nonylguanosine (2.1 g) was treated with bis-(N,N-diisopropylamino)-2-cyanoethyl-phosphite (1.5 g) and N,N-diisopropylammonium tetrazolide (0.2 g) as per the procedure of Example 6 to yield the product (2.0 g). $^{31}$P NMR (CDCl$_3$) δ 150.7 and 150.4 (diastereomers).

Example 17

2,6-Diamino-9-(2',3'-di-O-propyl-β-D-ribofuranosyl]purine

The procedure of Example 2 was repeated utilizing 2,6-diamino-9-(β-D-ribofuranosyl)purine (10 g), NaH (3 g) and 1-bromopropane (10 ml) in DMF. After evaporation of the reaction solvent, the reaction products were purified by silica gel chromatography. The slower moving component yielded 4.3 g of the 2'-O-propyl product as a foam. This foam was crystallized from water to yield 3.6 g of product. The faster moving component isolated as an oil formed crystals upon standing. EtOH was added to the crystals, they were filtered and wash 1×EtOH to yield 1.1 grams of 2',3'-di-O-propyl product. m.p. 165–167° C. $^1$H NMR (DMSO-d$_6$) δ 0.80 and 0.92 (t, 6, CH$_3$), 1.6 and 1.45 (m, 4, CH$_2$), 3.7–3.45 (br m, 6), 4.07 (m, 2), 4.5 (dd, 1), 5.55 (br t, 1, 5'-OH), 5.8 (br s, 2, 6-NH$_2$), 5.85 (d, 1, H-1'), 6.84 (br s, 2, 2-NH$_2$) and 8.0 (s, 1, H-8). Anal. Calcd. for C$_{16}$H$_{26}$N$_6$O$_4$: C, 52.45; H, 7.15; N, 22.94. Found: C, 52.18; H, 7.19; N, 22.75.

Example 18

N2,N6-Diisobutyryl-2,6-diamino-9-(2'-O-propyl-δ-D-ribofuranosyl)purine 2,6-diamino-9-(2'-O-propyl-β-D-ribofuranosyl)purine (2.0 g) in pyridine (35 ml) was treated with trimethylsilyl chloride (3.9 ml, 5 eq) and isobutyryl chloride (3.2 ml, 5 eq) as per the procedure of Example 4 to yield a foam after silica gel chromatography. The foam was crystallized from EtOAc/Hex to yield 2.2 g of product. m.p. 140–142° C. $^1$H NMR (DMSO-$d_6$) δ 0.77 (t, 3, C$\underline{H}_3$), 1.07, 1.16 [d, 12, 2× CH(C$\underline{H}_3)_2$], 1.5 (m, 2, C$\underline{H}_2$), 2.9, 3.03 [m, 2, 2× C$\underline{H}$(CH$_3)_2$], 3.4 (m, 1, $\underline{H}$-5"), 3.58 (m, 3, OC$\underline{H}_2$, $\underline{H}$-5'), 3.95 (m, 1, $\underline{H}$-4'), 4.3 (m, 1), 4.5 (m, 1), 5.02 (t, 1, 5'-O$\underline{H}$), 5.2 (d, 1, 3'-O$\underline{H}$), 6.03 (d, 1, $\underline{H}$-1'), 8.58 (s, 1, $\underline{H}$-8), 10.39 (br s, 1, N$\underline{H}$), and 10.57 (br s, 1, N$\underline{H}$).

Example 19

N2,N6-Diisobutyryl-2,6-diamino-9-(5'-O-dimethoxytrityl-2'-O-propyl-β-D-ribofuranosyl)purine N2,N6-Diisobutyryl-2,6-diamino-9-(2'-O-propyl-β-D-ribo-furanosyl)purine (1.9 g) was treated with dimethoxytrityl chloride (1.5 g, 1.1 eq), and dimethylaminopyridine (20 mg as a catalyst) in pyridine (50 ml) as per the procedure of Example 5 to yield the product as a foam (2.8 g). $^1$H NMR (DMSO-$d_6$) δ 0.79 (t, 3, C$\underline{H}_3$), 1.07, 1.16 [d, 12, 2× CH(C$\underline{H}_3)_2$], 1.5 (m, 2, C$\underline{H}_2$), 2.9, 3.03 (m, 2, 2×C$\underline{H}$(CH$_3)_2$], 3.58 (m, 3, OC$\underline{H}_2$, $\underline{H}$-5'), 4.15 (m, 1, $\underline{H}$-4'), 4.4 (m, 1), 4.6 (m, 1), 5.15 (d, 1, 3'-O$\underline{H}$), 6.15 (d, 1, $\underline{H}$-1'), 6. 8–7.35 (m, 13, DMTr), 8.5 (s, 1, $\underline{H}$-8), 10.3 (br s, 1, N$\underline{H}$), and 10.57 (br s, 1, N$\underline{H}$).

Example 20

N2,N6-Diisobutyryl-2,6-diamino-9-(5'-O-dimethoxytrityl-2'-O-propyl-β-D-ribofuranosyl)purine 3'-β-cyanoethyl-N,N-diisopropylphosphoramidite N2,N6-Diisobutyryl-2,6-diamino-9-(5'-O-dimethoxytrityl-2'-O-propyl-β-D-ribofuranosyl)purine (2.6 g) was treated with bis-(N,N-diisopropylamino)-2-cyanoethylphosphite (1.7 g) and N,N-diisopropylammonium tetrazolide (300 mg) overnight at room temperature. The reaction mixture was partitioned against dil. Na$_2$CO$_3$/CHCl$_2$ and then Na$_2$CO$_3$/NaCl and dried over MgSO$_4$. The organic layer was evaporated to a foam. The foam was dissolved in CH$_2$Cl$_2$ (≈8 ml) and slowly added to Hexanes (500 ml). The solid was filtered and dried to yield the product as a powder (3.1 g). $^{31}$P NMR (CDCl$_3$) δ 150.8 and 151.3.

Example 21

2,6-Diamino-9-[2'-O-[(N-phthalimido)prop-3-yl]-β-D-ribofuranosyl]purine & 2,6-Diamino-9-[3'-O-[(N-phthalimido)prop-3-yl]-β-D-ribo-furanosyl]purine 2,6-Diamino-9-(β-D-ribofuranosyl)purine (14.2 g) was treated with sodium hydride (3 g, 1.5 eq) and N-(3-bromopropyl)phthalimide (5.3 ml, 1.5 eq) in DMF (20 g) at 70° C. overnight. The reaction mixture was proportioned between H$_2$O and Hexanes (1×) and the aqueous layer then extracted 4× CH$_2$Cl$_2$. The organic layer was dried over MgSO$_4$ and evaporated to a residue. The residue was purified by silica gel chromatography eluted with MeOH/CH$_2$Cl$_2$. The 2'-O-(N-phthalimido)propyl product eluted first followed by mixed fractions and then the 3'-O-(N-phthalimido) product. Evaporations of the fractions gave 3.4 g of the 2'-O-(N-phthalimido)propyl product, 3.0 g of mixed 2' and 3' products and 1.4 g of the 3'-O-(N-phthalimido) propyl product all as foams. The 3'-O-(N-phthalimido) propyl product was crystallized from EtOAc/MeOH to give 270 mg of solid.

2,6-Diamino-9-[2'-O-[(N-phthalimido)prop-3-yl]-β-D-ribofuranosyl]purine $^1$H NMR (DMSO-$d_6$) δ 1.8 (tq, 2, —C$\underline{H}_2$—), 3.4–3.58 (m, 6, 2× C$\underline{H}_2$, $\underline{H}$-5'), 3.9 (m, 1), 4.26 (m, 1), 4.37 (m, 1), 5.05 (br d, 1, 3'-O$\underline{H}$), 5.4 (br t, 1, 5'-O$\underline{H}$), 5.72 (br s, 2, N$\underline{H}_2$), 5.8 (br d, 1, $\underline{H}$-1'), 6.75 (br s, 2, N$\underline{H}_2$), 7.8 (br s, 4, Ar) and 8.93 (s, 1, $\underline{H}$-8).

2,6-Diamino-9-[3'-O-[(N-phthalimido)prop-3-yl]-β-D-ribofuranosyl]purine m.p. 220–222° C., $^1$H NMR (DMSO-$d_6$) δ 1.85 (tq, 2, —C$\underline{H}$—N), 3.6–3.67 (m, 4, —O—C$\underline{H}_2$, $\underline{H}$-5'), 3.85 (m, 1), 3.92 (m, 1), 4.6 (m, 1), 5.33 (d, 1, 2'-O$\underline{H}$), 5.45 (br t, 1, 5'-O$\underline{H}$), 5.65 (d, 1, $\underline{H}$-1'), 5.73 (br s, 2, N$\underline{H}_2$), 6.75 (br d, 2, N$\underline{H}_2$), 7.8–7.85 (m, 4, Ar) and 7.85 (s, 1, $\underline{H}$-8). Anal. Calcd. for C$_{21}$H$_{23}$N$_7$O$_6$: C, 53.73; H, 4.94; N, 20.88. Found: C, 53.59; H, 4.89; N, 20.63.

Example 22

2'-O-[(N-Phthalimido)prop-3-yl]guanosine 2,6-diamino-9-[2'-O-[(N-phthalimido)prop-3-yl]-β-D-ribofuranosyl]purine (3.1 g) in 0.1 M sodium phosphate buffer (3 ml, pH 7.4), 0.05 M tris buffer (65 ml, pH 7.4) and DMSO (45 ml) was treated with adenosine deaminase (200 mg) at room temperature for 5 days as per the procedure of Example 3. The product containing fractions from the silica gel chromatography were evaporated and upon concentration formed white crystals. The crystals were filtered and washed with MeOH to yield 1.1 g of product. An analytical sample was recrystallized from MeOH. m.p. 192–194° C. $^1$H NMR (DMSO-$d_6$) δ 1.82 (m, 2, C$\underline{H}_2$), 3.45–3.67 (m, 6, $\underline{H}$-5', OC$\underline{H}_2$, NC$\underline{H}_2$), 3.9 (m, 1), 4.3 (m, 2, $\underline{H}$-2', $\underline{H}$-3'), 5.1 (m, 2, 5' and 3'-O$\underline{H}$), 5.8 (d, 1, $\underline{H}$-1'), 6.5 (br s, 2, N$\underline{H}_2$), 7.83 (s, 4, phthal), 7.98 (s, 1, $\underline{H}$-8) and 10.5 (br s, 1, N$\underline{H}$). Anal. Calcd. for C$_{21}$H$_{22}$N$_6$O$_7$·½H$_2$O: C, 52.61; H, 4.83; N, 17.53. Found: C, 52.52; H, 4.78; N. 17.38.

Example 23

N2-Isobutyryl-2'-O-[(N-phthalimido)prop-3-yl]guanosine

2'-O-(N-phthalimido)prop-3-yl]guanosine (7.2 g crude) in pyridine (35 ml) was treated with trimethylsilyl chloride (11.6 ml, 5 eq) and isobutyryl chloride (8 ml, 5 eq) as per the procedure of Example 4 to yield the product as a crude foam (6.5 g). An analytical sample was obtained by crystallization from EtOAc. m.p. 166–168° C. $^1$H NMR (DMSO-$d_6$) δ 1.15 [d, 6, —CH(C$\underline{H}_3)_2$], 1.85 (m, 2, C$\underline{H}_2$), 2.8 [m, 1, C$\underline{H}$(CH$_3)_2$], 3.45–3.7 (m, 6, H-5', OC$\underline{H}_2$, NC$\underline{H}_2$), 3.95 (m, 1), 4.34 (m, 1), 4.4 (m, 1), 5.12 (t, 1, 5'-O$\underline{H}$), 5.18 (d, 1, 3'-O$\underline{H}$), 5.9 (d, 1, $\underline{H}$-1'), 7.83 (s, 4, phthal), 8.3 (s, 1, $\underline{H}$-8), 11.65 (br s, 1, N$\underline{H}$) and 12.1 (br s, 1, N$\underline{H}$). Anal. Calcd. for C$_{25}$H$_{28}$N$_6$O$_8$·½H$_2$O: C, 54.64; H, 5.32; N, 15.29. Found: C, 54.46; H, 5.39; N, 14.98.

Example 24

N2-Isobutyryl-5'-dimethoxytrityl-2'-O-[(N-phthalimido)prop-3-yl]guanosine

N2-Isobutyryl-2'-O-[(N-phthalimido)prop-3-yl] guanosine (1.2 g) was treated with dimethoxytrityl chloride (820 mg, 1.1 eq), and dimethylaminopyridine (20 mg as a catalyst) in pyridine (50 ml) as per the procedure of Example 5 utilizing 1:1 Hex/EtOAc, then EtOAc then 5% MeOH/EtOAc with 1% TEA as eluent. The product containing fraction were evaporated to yield the product as a foam (1.7 g). $^1$H NMR (DMSO-$d_6$) δ 1.1 [d, 6, —CH(C$\underline{H}_3$)$_2$], 1.85 (m, 2, C$\underline{H}_2$), 2.75 [m, 1, C$\underline{H}$(CH$_3$)$_2$], 3.45–3.7 (m, 6, H-5', OC$\underline{H}_2$, NC$\underline{H}_2$), 3.75 (s, 6, OC$\underline{H}_3$), 4.0 (m, 1), 4.32 (m, 1), 4.4 (m, 1), 5.2 (d, 1, 3'-O$\underline{H}$), 5.93 (d, 1, $\underline{H}$-1'), 6.83, 7.2, 7.35 (a, 13, DMTr), 7.78 (s, 4, phthal), 8.15 (s, 1, $\underline{H}$-8), 11.6 (br s, 1, N$\underline{H}$) and 12.05 (br s, 1, N$\underline{H}$). Anal. Calcd. for C$_{46}$H$_{46}$N$_6$O$_{10}$.H$_2$O: C, 64.18; H, 5.62; N, 9.76. Found: C, 64.42; H, 5.78; N, 9.53.

Example 25

N2-Isobutyryl-5'-dimethoxytrityl-2'-O-[(N-phthalimido)prop-3-yl]guanosine 3'-β-cyanoethyl-N,N-diisopropylphosphoramidite N2-Isobutyryl-5'-dimethoxytrityl-2'-O-[(N-phthalimido)prop-3-yl]guanosine (1.6 g) was treated with bis-(N,N-diisopropylamino)-2-cyanoethylphosphite (1.48 g) and N,N-diisopropylammonium tetrazolide (200 mg) as per the procedure of Example 6 to yield the product (2.0 g). $^{31}$P NMR (CDCl$_3$) δ 150.9.

Example 26

N2-Dimethylaminomethylidene-5'-dimethoxytrityl-2'-O-(N-phthalimido)prop-3-yl]guanosine 2'-O-[(N-phthalimido)prop-3-yl]guanosine (900 mg) in DMF (20 ml) was treated with N,N-dimethylformamide dimethyl acetal (2 ml). The reaction mixture was stirred for 2 hr and evaporated under high vac at 52° C. The residue was co-evaporated 1× with pyridine and taken up in solution in pyridine. Dimethoxytrityl chloride (713 mg, 1.1 eq) and dimethylaminopyridine (20 mg as a catalyst) were added. The reaction mixture was stirred overnight, partitioned between Na$_2$CO$_3$/CH$_2$Cl$_2$, dried over MgSO$_4$ and purified by silica gel chromatography as per the procedure of Example 5 to yield 1.7 g of product as an off white solid. $^1$H NMR (DMSO-$d_6$) δ 1.88 (m, 2, C$\underline{H}_2$), 3.1 [d, 6, N=CHN(C$\underline{H}_3$)$_2$], 3.3 (m, 2, $\underline{H}$-5'), 3.67 (m, 4, OC$\underline{H}_2$, NC$_2$), 3.78 (s, 6, 2× OC$\underline{H}_3$), 4.0 (m, 1, $\underline{H}$-4'), 4.35 (m, 2, $\underline{H}$-2', $\underline{H}$-3'), 5.2 (d, 1, 3'-O$\underline{H}$), 5.95 (d, 1, $\underline{H}$-1'), 6.85, 7.25, 7.39 (m, 13, DMTr), 7.85 (s, 4, phthal), 7.95 [s, 1, $\underline{H}$-8), 8.5 (s, 1, N=C$\underline{H}$N(CH$_3$)$_2$] and 11.39 (s, 1, N$\underline{H}_2$). Anal. Calcd. for C$_{45}$H$_{45}$N$_7$O$_9$.½H$_2$O: C, 64.58; H, 5.54; N, 11.71. Found: C, 64.10; H, 5.65; N, 11.47.

Example 27

N2-Dimethylaminomethylidene-5'-dimethoxytrityl-2'-O-[(N-phthalimido)prop-3-yl]guanosine 3'-β-cyanoethyl-N,N-diisopropylphosphoramidite N2-dimethylaminomethylidene-5'-dimethoxytrityl-2'-O-[(N-phthalimido)prop-3-yl]guanosine (1.7 g), bis-(N,N-diisopropylamino)-2-cyanoethylphosphite (1.4 ml) and N,N-diisopropylammonium tetrazolide (170 mg) were stirred overnight at room temperature. The reaction mixture was partitioned between CH$_2$Cl$_2$ and Na$_2$CO$_3$ (2×). The organic phase was dried over MgSO$_4$ and evaporated to an oil. The oil was dissolved in a minimum of CH$_2$Cl$_2$ and added dropwise to ≈900 ml Hexanes to precipitate the product. The solid was isolated and dried to yield 2.1 g of product. $^1$P NMR (CDCl$_3$) δ 150.4, 150.6.

Example 28

2,6-Diamino-9-[2'-O-(N-phthalimido)pent-5-yl]-β-D-ribofuranosyl]purine 2,6-Diamino-(9-β-D-ribofuranosyl)purine (6.7 g) was treated with sodium hydride (1.3 g) and N-(5-bromopentyl) phthalimide (7.8 g, 1.1 eq) in DMF (60 ml) at room temperature for three days. The reaction mixture was proportioned between H$_2$O and CH$_2$Cl$_2$ and extracted 4× CH$_2$Cl$_2$. The combined organic layers were dried over MgSO$_4$ and evaporated. The residue was purified by silica gel chromatography eluted with 5→10% MeOH/CH$_2$Cl$_2$. The 2'-O-(N-phthalimido)pentyl containing fractions were collected and evaporated to a yellow foam to give 2.2 g of product. An analytical sample was crystallized from EtOH. m.p. 173–175° C. $^1$H NMR (DMSO-$d_6$) δ 1.2 (m, 2, —C$\underline{H}_2$—), 1.47 (m, 4, 2× C$\underline{H}_2$), 3.55, 3.65 (m, 6, O—C$\underline{H}_2$, $\underline{H}$-5', NC$\underline{H}_2$), 3.95 (m, 1), 4.28 (m, 1), 4.4 (m, 1), 5.13 (d, 1, 3'-O$\underline{H}$), 5.5 (t, 1, 5'-O$\underline{H}$), 5.77 (br s, 2, 6-N$\underline{H}_2$), 5.84 (br d, 1, $\underline{H}$-1'), 6.8 (br s, 2, 2-N$\underline{H}_2$), 7.86 (M, 4, phthal) and 7.95 (s, 1, $\underline{H}$-8). Anal. Calcd. for C$_{23}$H$_{27}$N$_7$O$_6$: C, 55.50; H, 5.47; N, 19.71. Found: C, 55.44; H, 5.51; N, 19.30.

Example 29

2'-O-[(N-Phthalimido)pent-5-yl]guanosine

A mixture of the 2,6-diamino-9-[2'-O-[(N-phthalimido) pent-5-yl]-β-D-ribofuranosyl]purine and 2,6-diamino-9-[3'-O-[(N-phthalimido)pent-5-yl]-β-D-ribofuranosyl]purine isomers (2.2 g) in 0.1 M tris buffer (60 ml, pH 7.4), 0.1 M NaPO$_4$ buffer (2 ml, pH 7.4) and DMSO (40 ml) was treated with adenosine deaminase (60 mg) at room temperature for 5 days as per the procedure of Example 3. The product containing fractions from the silica gel chromatography were evaporated to give the product (1.0 g) as a crude white solid. An analytical sample was prepared by the addition of MeOH to form crystals. m.p. 178–180° C. $^1$H NMR (DMSO-$d_6$) δ 1.24 (m, 2, C$\underline{H}_2$), 1.5 (m, 4, 2× C$\underline{H}_2$), 3.5–3.6 (m, 6, $\underline{H}$-5', OC$\underline{H}_2$, NC$\underline{H}_2$), 3.87 (m, 1, $\underline{H}$-4'), 4.25 (m, 2, $\underline{H}$-2', $\underline{H}$-3'), 5.1 (m, 2, 5' and 3'-O$\underline{H}$), 5.78 (d, 1, $\underline{H}$-1'), 6.5 (br s, 2, N$\underline{H}_2$), 7.84 (M, 4, phthal), 7.98 (s, 1, $\underline{H}$-8) and 10.67 (br s, 1, N$\underline{H}$). Anal. Calcd. for C$_{23}$H$_{26}$N$_6$O$_7$.½H$_2$O: C, 54.43; H, 5.36; N, 16.56. Found: C, 54.79; H, 5.24; N, 16.61.

Example 30

N2-Isobutyryl-2'-O-[(N-phthalimido)pent-5-yl] guanosine

2'-O-[(N-phthalimido)pent-5-yl)guanosine (1.6 g, crude) in pyridine (35 ml) was treated with trimethylsilyl chloride (2.0 ml, 5 eq) and isobutyryl chloride (1.68 ml, 5 eq) as per the procedure of Example 4 to yield the product as a foam. This foam was co-evaporated 2× with EtOAc followed by the addition of EtOAc and heating to yield white crystals (950 mg). m.p. 202–204° C. $^1$H NMR (DMSO-$d_6$) δ 1.1 [d, 6, —CH(C$\underline{H}_3$)$_2$], 1.17 (m, 2, C$\underline{H}_2$), 1.43 (m, 4, 2× C$\underline{H}_2$), 2.74 [m, 1, C$\underline{H}$(CH$_3$)$_2$], 3.45–3.55 (m, 6, H-5', OC$\underline{H}_2$, NC$\underline{H}_2$), 3.9 (m, 1), 4.25 (m, 1), 4.3 (m, 1), 5.07 (t, 1, 5'-O$\underline{H}$), 5.15 (d, 1, 3'-O$\underline{H}$), 5.87 (d, 1, $\underline{H}$-1'), 7.8 (s, 4, phthal), 8.27 (s, 1, $\underline{H}$-8), 11.67 (br s, 1, N$\underline{H}$) and 12.06 (br s, 1, N$\underline{H}$). Anal. Calcd. for C$_{27}$H$_{32}$N$_6$O$_8$.½H$_2$O: C, 56.14; H, 5.76; N, 14.55. Found: C, 56.45; H, 5.74; N, 14.41.

Example 31

N2-Isobutyryl-5'-dimethoxytrityl-2'-O-[(N-phthalimido)pent-5-yl]guanosine

N2-Isobutyryl-2'-O-[(N-phthalimido)pent-5-yl] guanosine (0.95 g) was treated with dimethoxytrityl chloride (620 mg, 1.1 eq), and dimethylaminopyridine (20 mg as a catalyst) in pyridine (50 ml) as per the procedure of Example 5 utilizing EtOAc 1% TEA and then 5%. MeOH EtOAc/ $CH_2Cl_2$ with 1% TEA as eluent. The product containing fractions were evaporated to yield the product as a foam (1.4 g). $^1$H NMR (DMSO-$d_6$) δ 1.14 (d, 6, —CH(CH$_3$)$_2$], 1.25 (m, 2, CH$_2$), 1.53 (m, 4, 2× CH$_2$), 2.77 [m, 1, CH(CH$_3$)$_2$], 3.3–3.6 (m, 6, H-5', OCH$_2$, NCH$_2$), 3.75 (s, 6, OCH$_3$), 4.07 (m, 1), 4.33 (m, 1), 4.4 (m, 1), 5.18 (d, 1, 3'-OH), 5.94 (d, 1, H-1'), 6.83, 7.2, 7.53 (m, 13, DMTr), 7.8 (s, 4, phthal), 8.15 (s, 1, H-8), 11.6 (br s, 1, NH) and 12.1 (br s, 1, NH). Anal. Calcd. for $C_{48}H_{50}N_6O_{10}$·½$H_2O$: C, 65.52; H, 5.84; N, 9.55. Found: C, 65.55; H, 5.94; N, 9.20.

Example 32

2,6-Diamino-9-[3',5'-O-(tetraisopropyldisiloxane-1, 3-diyl)-β-D-ribofuranosyl]purine To a suspension of 2,6-diamino-9-(β-D-ribofuranosyl) purine (10.5 g) in pyridine (100 ml) was added 1,3-dichlorotetraisopropyldisiloxane (TIPDS, 12.6 g). The reaction was stirred at room temperature for 4 hours and an additional 1.3 g of 1,3-dichlorotetraisopropyldisiloxane was added followed by stirring overnight. The reaction mixture was poured into ice water and the insoluble product (11.6 g) collected by filtration. An analytical sample was recrystallized from EtOAc/Hexanes. m.p. 170–172° C. Anal. Calcd. for $C_{22}H_{40}N_6O_5Si_2$·½$H_2O$: C, 49.5; H, 7.74; N, 15.7. Found: 49.57; H, 7.82; N, 15.59.

Example 33

2,6-Diamino-9-[3',5'-O-(tetraisopropyldisiloxane-1, 3-diyl)-2-O-methyl-β-D-ribofuranosyl]purine A mixture of 2,6-Diamino-9-[3,5-O-(tetraisopropyldisiloxane-1,3-diyl)-β-D-ribofuranosyl] purine (8.8 g) in DMF (120 ml) and methyl iodide (3 ml, 3 eq) was cooled in an ice bath and NaH (60% in oil, 1.0 g, 1.5 eq) added. After 20 min the reaction was quenched with MeOH and partitioned between sat. NH$_4$Cl and CH$_2$Cl$_2$. The organic phase was washed with 1×NH$_4$Cl, dried over MgSO$_4$ and evaporated. The residue was crystallized from hot EtOH/H$_2$O to yield the product (8.5 g) as crystals. m.p. 87–89° C. $^1$H NMR (DMSO-$d_6$) δ 1.05 (m, 28, TIPDS), 3.57 (s, 3, OCH$_3$), 3.98 (m, 1, H-4'), 3.92 and 4.07 (ABX, 2, H-5'), 4.13 (d, 1), 4.6 (dd, 1, H-3'), 5.76 (br s, 2, NH$_2$), 5.8 (s, 1, H-1'), 6.77 (br s, 2, NH$_2$) AND 7.77 (s, 1 H-8)

Example 34

2,6-Diamino-9-(2'-O-methyl-β-D-ribofuranosyl) purine

To a solution of 2,6-Diamino-9-[3',5'-O-(tetraisopropyldisiloxane-1,3-diyl)-2'-O-methyl-β-D-ribofuranosyl]purine (8.5 g) in THF (50 ml) was added 1M tetrabutylammonium fluoride in THF (Aldrich, 20 ml). The reaction mixture was stirred for 2 hrs and filtered. The filter cake was washed with 2×EtOAc and air dried to give 4.0 g of crude product. An analytical sample was crystallized from hot MeOH. m.p. 133–135° C. $^1$H NMR (DMSO-$d_6$) δ 3.3 (s, 3, OCH$_3$), 3.58 (m, 2, H-5'), 3.98 (m, 1, H-4'), 4.28 (m, 2, H-2', H-3'), 5.23 (br s, 1, 3'-OH), 5.48 (br t, 1, 5'-OH), 5.77 (br s, 2, NH$_2$), 5.82 (d, 1, H-1'), 6.83 (br s, 2, NH$_2$) and 7.95 (s, 1, H-8). Anal. Calcd. for $C_{11}H_{16}N_6O_4$·½$H_2O$: C, 43.28; H, 5.61; N, 27.52. Found: C, 43.51; H, 5.62; N, 27.26.

Example 35

2'-O-Methylguanosine 2,6-Diamino-9-(2'-O-methyl-β-D-ribofuranosyl)purine (9.5 g) in 0.1M sodium phosphate buffer (200 ml, pH 7.4) and DMSO (25 ml) was treated with adenosine deaminase (Type II Sigma) at RT for 4 days. The resulting suspension was cooled and filtered and the resulting filter cake washed with H$_2$O and dried to a white solid (4.0 g). The solid was recrystallized from hot H$_2$O to yield 2.9 g of product. m.p. 236–238° C. $^1$H NMR (DMSO-$d_6$) δ 3.3 (s, 3, OCH$_3$), 3.53 and 3.6 (ABX, 2, H-5'), 3.87 (m, 1, H-4'), 4.15 (m, 1, H-2'), 4.25 (m, 1, H-3'), 5.13 (t, 1, 5'-OH), 5.23 (d, 1, 3'-OH), 5.8 (d, 1, H-1'), 6.48 (br s, 2, NH$_2$), 7.96 (s, 1, H-8) and 10.68 (br s, 1, NH). Anal. Calcd. for $C_{11}H_{15}N_5O_5$·½$H_2O$: C, 43.14; H, 5.26; N, 22.86. Found: C, 43.59; H, 5.34; N, 23.04.

Example 36

N2-Isobutyryl-2'-O-methylguanosine

2'-O-methylguanosine (3.5 g) in pyridine (100 ml) was treated with trimethylsilyl chloride (9 ml, 6 eq) and isobutyryl chloride (6.2 ml) at RT for 4 hr. The reaction mixture was cooled in an ice bath, H$_2$O (20 ml) was added and stirring continued for an additional 20 min. NH$_4$OH (20 ml) was added and after stirring for 30 min the reaction mixture was evaporated. The residue was triturated with H$_2$O, filtered and the filtrate evaporated and purified by silica gel chromatography as per the procedure of Example 4 to yield the product as an off white solid (1.5 g). $^1$H NMR (DMSO-$d_6$) δ 1.1 [d, 6, CH(CH$_3$)$_2$], 2.77 [m, 1, CH(CH$_3$)$_2$], 3.33–3.6 (m, 5, OCH$_3$, H-5'), 3.93 (m, 1, H-4'), 4.22 (m, 1), 4.3 (m, 1), 5.1 (t, 1, 5'-OH), 5.28 (d, 1, 3'-OH), 5.9 (d, 1, H-1'), 8.28 (s, 1, H-8) and 11.9 (br s, 1, NH).

Example 37

N2-Isobutyryl-5'-dimethoxytrityl-2'-O-methylguanosine

N2-Isobutyryl-2'-O-methylguanosine (1.5 g) was treated with dimethoxytrityl chloride (1.5 g, 1.1 eq), and dimethylaminopyridine (100 mg as a catalyst) in pyridine (50 ml) as per the procedure of Example 5 to yield the product as a foam (2.6 g). $^1$H NMR (DMSO-$d_6$) δ 1.14 (d, 6, CH(CH$_3$)$_2$], 2.75 [m, 1, CH(CH$_3$)$_2$], 3.5 (m, 2, H-5'), 3.74 (s, 6, OCH$_3$), 4.05 (m, 1), 4.33 (m, 1), 5.26 (d, 1, 3'-OH), 5.95 (d, 1, H-1'), 6.83, 7.2, 7.35 (m, 13, DMTr), 8.15 (s, 1, H-8), 11.6 (br s, 1, NH) and 12.1 (br s, 1, NH).

Example 38

N2-Isobutyryl-5'-dimethoxytrityl-2'-O-methylguanosine 3'-β-cyanoethyl-N,N-diisopropylphosphoramidite N2-Isobutyryl-5'-dimethoxytrityl-2'-O-methylguanosine (20 g) was treated with bis-(N,N-diisopropylamino)-2-cyanoethylphosphite (10.8 g) and N,N-diisopropylammonium tetrazolide (1.6 g) as per the procedure of Example 6 to yield the product (15.7 g). $^{31}$P-NMR (CDCl$_3$) δ 148.97 and 147.96.

Example 39

N2,N6-Diisobutyryl-2,6-diamino-9-(2'-O-methyl-β-D-ribofuranosyl)purine 2,6-diamino-9-(2'-O-methyl-β-D-ribofuranosyl)purine (700 mg) in pyridine (20 ml) was treated with trimethylsilyl chloride (2.1 ml, 7 eq) and isobutyryl chloride (1.25 ml, 5 eq) as per the procedure of Example 4 to yield the product as a foam (900 mg) after silica gel chromatography.

Example 40

N2,N6-Diisobutyryl-2,6-diamino-9-(5'-O-dimethoxytrityl-2'-O-methyl-β-D-ribofuranosyl) purine N2,N6-Diisobutyryl-2,6-diamino-9-(5'-O-methyl-β-D-ribofuranosyl)purine (900 mg) was treated with dimethoxytrityl chloride (1.0 g) and dimethylaminopyridine (20 mg as a catalyst) in pyridine (30 m) as per the procedure of Example 5 to yield the product as a foam (700 mg). $^1$H NMR (DMSO-$\underline{d}_6$) δ 0.96–1.16 [m, 12, 2× CH(C$\underline{H}_3$)$_2$], 2.9 and 3.05 [M, 2, 2× C$\underline{H}$(CH$_3$)$_2$], 3.18 and 3.37 (ABX, 2, $\underline{H}$-5'), 3.38 (s, 3, OC$\underline{H}_3$), 3.7 (s, 6, OC$\underline{H}_3$), 4.05 (m, 1, H-4'), 4.44 (m, 2, $\underline{H}$-2', $\underline{H}$-3'), 5.24 (d, 1, 3'-O$\underline{H}$), 6.06 (d, 1, $\underline{H}$-1'), 6.78, 7.2, 7.33 (m, 13, Ar), 8.22 (s, 1, $\underline{H}$-8), 10.3 (br s, 1, N$\underline{H}$) and 10.57 (br 6, 1, N$\underline{H}$).

Example 41

N2,N6-Diisobutyryl-2,6-diamino-9-(5'-O-dimethoxytrityl-2'-O-methyl-β-D-ribofuranosyl) purine 3'-β-cyanoethyl-N,N-diisopropylphosphoramidite N2,N6-Diisobutyryl-2,6-diamino-9-(5'-O-dimethoxytrityl-2'-O-methyl-β-D-ribofuranosyl)purine (600 mg,) was treated with bis-(N,N-diisopropylamino)-2-cyanoethylphosphite (500 μl) and N,N-diisopropylammonium tetrazolide (80 mg) overnight at RT. The reaction mixture was partitioned against dil. Na$_2$CO$_3$/CHCl$_2$ and then Na$_2$CO$_3$/NaCl and dried over MgSO$_4$. The organic layer was evaporated to a foam (500 mg). $^{31}$P NMR (CDCl$_3$) δ 151.1 (doublet).

Example 42

2,6-Diamino-9-(2'-O-octadecyl-β-D-ribofuranosyl) purine 2,6-Diamino-9-(β-D-ribofuranosyl)purine (50 g, 180 mmol) and sodium hydride (7 g) in DMF (1 l) were heated to boiling for 2 hr. Iodooctadecane (100 g) was added at 150° C. and the reaction mixture allowed to cool to RT. The reaction mixture was stirred for 11 days at RT. The solvent was evaporated and the residue purified by silica gel chromatography. The product was eluted with 5% MeOH/CH$_2$Cl$_2$. The product containing fraction were evaporated to yield the product (11 g). $^1$H NMR (DMSO-$\underline{d}_6$) δ 0.84 (t, 3, C$\underline{H}_3$); 1.22 [m, 32, O—CH$_2$—CH$_2$—(C$\underline{H}_2$)$_{16}$—]; 1.86 (m, 2, O—CH$_2$C$\underline{H}_2$—); 3.25 (m, 2, O—C$\underline{H}_2$—); 3.93 (d, 1, 4'$\underline{H}$), 4.25 (m, 1, 3'$\underline{H}$); 4.38 (t, 1, 2'$\underline{H}$); 5.08 (d, 1, 3'-O$\underline{H}$); 5.48 (t, 1, 5'-O$\underline{H}$); 5.75 (s, 2, 6-N$\underline{H}_2$); 5.84 (d, 1, 1'-$\underline{H}$); 6.8 (s, 2, 2-N$\underline{H}_2$); and 7.95 (s, 1, 8-$\underline{H}$).

Example 43

2'-O-Octadecylguanosine 2,6-Diamino-9-(2'-O-octadecyl-β-D-ribofuranosyl) purine (10 g) in 0.1 M sodium phosphate buffer (50 ml, pH 7.4), 0.1 M tris buffer (1000 ml, pH 7.4) and DMSO (1000 ml) was treated with adenosine deaminase (1.5 g) as per the procedure of Example 3. At day 3, day 5 and day 7 an additional aliquot (500 mg, 880 mg and 200 mg, respectively) of adenosine deaminase was added. The reaction was stirred for a total of 9 day and after purification by silica gel chromatography yielded the product (2 g). An analytical sample was recrystallized from MeOH $^1$H NMR (DMSO-$\underline{d}_6$) δ 0.84 (t, 3, C$\underline{H}_3$), 1.22 [s, 32, O—CH$_2$—CH$_2$—(C$\underline{H}_2$)$_{16}$], 5.07 (m, 2, 3'-O$\underline{H}$5'-O$\underline{H}$); 5.78 (d, 1, 1'-$\underline{H}$); 6.43 (s, 2, N$\underline{H}_2$), 7.97 (s, 1, 8-$\underline{H}$) and 10.64 (s, 1, N$\underline{H}_2$). Anal. Calcd. for C$_{28}$H$_{49}$N$_5$O$_5$: C, 62.80; H, 9.16; N, 12.95. Found: C, 62.54; H, 9.18; N, 12.95.

Example 44

N2-Isobutyryl-2'-O-octadecylguanosine

2'-O-octadecylguanosine (1.9 g) in pyridine (150 ml) was treated with trimethylsilyl chloride (2 g, 5 eq) and isobutyryl chloride (2 g, 5 eq) as per the procedure of Example 4. The product was purified by silica gel chromatography (eluted with 3% MeOH/EtOAc) to yield 1.2 g of product. $^1$H NMR (DMSO-$\underline{d}_6$) δ 0.85 [t, 3, C$\underline{H}_3$], 1.15 [m, 38, O—CH$_2$CH$_2$(C$\underline{H}_2$)$_{16}$, CH(C$\underline{H}_3$)$_2$], 2.77 [m, 1, C$\underline{H}$(CH$_3$)$_2$], 4.25 (m, 2, 2'$\underline{H}$, 3'$\underline{H}$); 5.08 (t, 1, 5'-O$\underline{H}$), 5.12 (d, 1, 3'-O$\underline{H}$), 5.87 (d, 1, 1'-$\underline{H}$), 8.27 (s, 1, 8-$\underline{H}$), 11.68 (s, 1, N$\underline{H}_2$) and 12.08 (s, 1, N$\underline{H}_2$). Anal. Calcd. for C$_{32}$H$_{55}$N$_5$O$_6$: C, 63.47; H, 9.09; N, 11.57. Found: C, 63.53; H, 9.20; N, 11.52.

Example 45

2,6-Diamino-9-[2'-O-(imidazol-1-yl)butyl-β-D-ribofuranosyl]purine 2,6-Diamino-(9-β-D-ribofuranosyl)purine (5.0 g) in DMF (400 ml) was treated with sodium hydride (0.78 g). After stirring an additional 30 min a further portion of sodium hydride (2.6 g) was added immediately followed by bromobutyl-imidazole (9.9 g) in DMF (25 ml). The reaction mixture was stirred overnight and quenched with H$_2$O. The reaction mixture was filtered through celite and evaporated to yield an oily product. TLC showed a mixture of isomers.

Example 46

2'-O-(Imidazol-1-yl)butylguanosine

A mixture of the 2,6-diamino-9-[2'-O-(imidazol-1-yl) butyl-β-D-ribofuranosyl]purine and 2,6-diamino-9-[3'-O-(imidazol-1-yl)butyl-β-D-ribofuranosyl]purine isomers in 0.1 M tris buffer (pH 7.4), 0.1 M NaSO$_4$ buffer (pH 7.4) and DMSO is treated with adenosine deaminase at RT for 5 days as per the procedure of Example 3. The product containing fractions are purified by silica gel chromatography and the product containing fraction evaporated to give the product.

Example 47

N2-Isobutyryl-2'-O-(imidazol-1-yl)butylguanosine

2'-O-(imidazol-1-yl)butylguanosine in pyridine will be treated with trimethylsilyl chloride (5 eq) and isobutyryl chloride (5 eq) as per the procedure of Example 4 to yield the product.

Example 48

N2-Isobutyryl-5'-dimethoxytrityl-2'-O-(imidazol-1-yl)butylguanosine

N2-Isobutyryl-2'-O-(imidazol-1-yl)butylguanosine will be treated with dimethoxytrityl chloride (1.1 eq), and dimethylaminopyridine (as a catalyst) in pyridine as per the procedure of Example 5. After chromatography purification, the product containing fractions will be evaporated to yield the product).

Example 49

2',3'-O-Dibutylstannylene uridine

Utilizing the protocol of Wagner, et al., *J. Org. Chem.* 1974, 39, 24, uridine (45 g, 0.184 mol) was refluxed with di-n-butyltinoxide (45 g, 0.181 mol) in 1.4 l of anhydrous methanol for 4 hrs. The solvent was filtered and the resultant: 2',3'-O-dibutylstannylene-uridine was dried under vacuum at: 100° C. for 4 hrs to yield 81 g (93%).

Example 50

2'-O-[Pentyl-ω-(N-phthalimido)]uridine

2',3'-O-Dibutyl stannylene-uridine was dried over P$_2$O$_5$ under vacuum for 12 hrs. To a solution of this compound (20 g, 42.1 mmols) in 500 ml of anhydrous DMF were added 25 g (84.2 mmols) of N(5-bromopentyl)phthalimide (Trans World Chemicals, Rockville, Md.) and 12.75 g (85 mmols) of cesium fluoride (CsF). The mixture was stirred at room temperature for 72 hrs. The reaction mixture was evaporated then co-evaporated once with toluene and the residue was partitioned between EtOAc and water (400 ml each). The EtOAc layer was concentrated and applied to a silica column (700 g). Elution with $CH_2Cl_2$—$CH_3OH$ (20:1, v/v) gave fractions containing a mixture of the 2'- and 3'-isomers of O-pentyl-ω-N-phthalimido uridine, in 50% yield.

Example 51

5'-O-Dimethoxytrityl-2'-O-[pentyl-ω-(N-phthalimido)]uridine

The isomeric mixture of 2'-O-[pentyl-ω-(N-phthalimido)] uridine was allowed to react with DMT chloride in dry pyridine at room temperature for 6 hrs. $CH_3OH$ was used to quench excess DMT-Cl and the residue was partitioned between $CH_2Cl_2$ containing 0.5% $Et_3N$ and water. The organic layer was dried ($MgSO_4$) and the residue was applied to a silica column. The column was eluted with $CH_2Cl_2$:$CH_3OH$ (20:1, v/v) to separate the 2' and 3' isomers of the product.

Example 52

5'-O-Dimethoxytrityl-2'-O-[pentyl-ω-(N-phthalimido)]uridine-3'-O-(β-cyanoethyl N,N-diisopropylphosphoramidite)

5'-O-Dimethoxytrityl-2'-O-[pentyl-ω-(N-phthalimido)] uridine was placed in a dry round bottom flask containing a teflon stir-bar. The flask was purged with argon. Anhydrous methylene chloride was added to the flask in an amount sufficient to dissolve the nucleoside. Previously vacuum dried N,N-diisopropylaminohydrotetrazolide (600 mg, 0.014 mol) was added under argon. Bis-N,N-diisopropylamino-cyanoethylphosphite was added via syringe. The reaction was stirred under argon at 25° C. for 16 h. Upon completion of the reaction, the reaction was transferred to a separatory funnel. The reaction flask was rinsed with methylene chloride (2×50 mL). The combined organic layer was washed 2× with sat'd aq. sodium bicarbonate. The organic layer was dried over magnesium sulfate, evaporated and taken up in toluene containing 1% triethylamine. The resulting phosphoramidite was purified by silica gel flash chromatography and eluted with 3:1→1:1 Hexanes/ ethyl acetate containing it triethylamine. Selected fractions were combined, concentrated under reduced pressure and dried to yield the product as a white foam. $^{31}$P-NMR ($CDCl_3$, $H_3PO_4$ std.) showed the correct diastereomers

Example 53

2'-O-Pentyluridine

Utilizing the procedures of Examples 50 and 51, 2',3'-O-dibutylstannylene uridine (19.1 g) was treated with bromopentane (7 ml, 1.3 eq.) and sodium iodide (4.5 g) in DMF (90 ml). Purification on a silica gel column utilizing MeOH/ $CH_2Cl_2$ 5%→10% yielded the a mixture of 2' and 3' isomers of the product as a dark oil (9.8 g).

Example 54

5'-O-Dimethoxytrityl-2'-O-pentyluridine

The mixture of 2'-O-pentyluridine and 3'-O-pentyluridine (9.8 g) was reacted with dimethoxytrityl chloride (10.5 g) as per the procedure of Example 51. The crude product was purified on a silica gel column (1000 g). Elution with Hex.-EtOAc (3:1→1:1) gave 5.5 g of the 2'-O-pentyl isomer and 3 g of the 3'-O-pentyl isomer. Anal. Calcd. for $C_{35}H_{37}N_2O_8 \cdot \frac{1}{2}H_2O$: C, 67.51; H, 6.55; N, 4.5. Found: C, 67.48; H, 6.55; N, 4.5.

Example 55

5'-O-Dimethoxytrityl-2'-O-pentyluridine-3'-O-(β-cyanoethyl N,N-diisopropylphosphoramidite)

The protected 5'-O-dimethoxytrityl-2'-O-pentyluridine (4.6 g. 0.007 mol) was placed in a dry round bottom flask containing a teflon stir-bar. The flask was purged with argon. Anhydrous methylene chloride was added to the flask in an amount sufficient to dissolve the nucleoside. Previously vacuum dried N,N-diisopropylaminohydrotetrazolide (600 mg, 0.014 mol) was added under argon. Bis-N,N-diisopropylamino-cyanoethylphosphite (4.5 g, 4.7 ml, 2 eq.) was added with stirring via syringe. The reaction was stirred under argon at 25° C. for 16 h. After verifying the completion of the reaction by TLC, the reaction was transferred to a separatory funnel and the reaction flask was rinsed with methylene chloride (2×50 mL). The combined organic layer was washed 2× with sat'd aq. sodium bicarbonate. The organic layer was dried over magnesium sulfate, evaporated and taken up in toluene containing 1% triethylamine. The resulting phosphoramidite was purified by silica gel flash chromatography (300 g) and eluted with Hexanes/ethyl acetate (3:1→1:1 containing 1% triethylamine). Selected fractions were combined, concentrated under reduced pressure and dried to yield 2.67 g of product as a white foam. $^{31}$P-NMR ($CDCl_3$, $H_3PO_4$ std.) showed the correct diastereomers

Example 56

2'-O-Methyluridine

As per the procedure of Example 49, uridine (8.5 g) was treated with dibutyl tin oxide (8.2 g, 1 eq). The resulting 2',3'-O-dibutylstannylene uridine was treated with iodomethane (16 ml) at 42° C. as per Example 50 to give a mixture of the 2' and 3' alkylated products (3.5 g) as a foam.

Example 57

5'-O-(4,4'-Dimethoxytriphenylmethyl)-2'-O-methyluridine

2'-O-Methyluridine (8.0 g, 0.031 mol) was evaporated under reduced pressure with pyridine (100 mL) to an oil. To the residue was added 4,4'-dimethoxytriphenylmethyl chloride (DMT-Cl, 11.5 g, 0.34 mol) and pyridine (100 mL). The mixture was stirred at 25° C. for 1.5 h and then quenched by the addition of methanol (10 mL) for 30 min. The mixture was concentrated under reduced pressure and the residue was chromatographed on silica gel (250 g), Elution with hexanes-ethyl acetate-triethylamine (80:20:1) and then ethyl acetate-triethylamine (99:1). The appropriate fractions were combined, evaporated under reduced pressure and dried at 25° C./0.2 mmHg for 1 h to provide 17.4 g (100%) of tan foam; TLC purity 98% (Rf 0.23, hexanes-ethyl acetate 4:1); PMR (DMSO) d 11.4 (H—$N^3$), 7.78 (H-6), 7.6–6.8 (Bz), 5.8 (H-1'), 5.3 (H-5'), 5.25 (HO-3'), 3.7 ($CH_3O$-Bz), 3.4, ($CH_3O$-2').

Example 58

5'-O-(4,4'-dimethoxytriphenylmethyl)-2'-O-methyluridine-3'-O-(β-cyanoethyl N,N-diisopropylphosphoramidite)

The product was prepared as per Example 54 from the intermediate 5'-O-(4,4'-dimethoxytriphenylmethyl)-2'-O- methyl-uridine. Ethyl acetate-hexanes-triethylamine (59:40:1) was used as the chromatography eluent to give the product as a solid foam in 60% yield. TLC homogenous diastereomers, Rf 0.58; 0.44 [ethyl acetate-hexanes-triethylamine 59:40:1) ]. $^{31}$P-NMR (CDCl$_3$, H$_3$PO$_4$ std.) d 148.11; 148.61 (diastereomers).

Example 59

2'-O-Propyluridine

As per the procedure of Example 49, uridine (10 g) was treated with dibutyl tin oxide (10.2 g, 1 eq). The resulting 2',3'-O-dibutylstannylene uridine was treated with iodopropane (8 ml, 2 eq.) at 110° C. as per Example 50 to give a mixture of the 2' and 3' isomers (5.5 g) as a foam.

Example 60

5'-O-(4,4'-Dimethoxytriphenylmethyl)-2'-O-propyluridine

The mixture of 2'-O-propyluridine and 3'-O-propyluridine (3.6 g) was reacted with dimethoxytrityl chloride (4.2 g, 1.0 eq.) as per Example 51. The residue was chromatographed on silica gel eluted with Hex/EtOAc (1:1 with 1% triethylamine). The appropriate fractions were combined, evaporated under reduced pressure and dried to provide 4.2 g of a white foam. Anal. Calcd. for C$_{33}$H$_{36}$N$_2$O$_8$·½H$_2$O: C, 67.33; H, 6.16; N, 4.76. Found: C, 67.15; H, 6.24; N, 4.44.

Example 61

5'-O-(4,4'-dimethoxytriphenylmethyl)-2'-O-propyluridine-3'-O-(β-cyanoethyl N,N-diisopropylphosphoramidite)

The product was prepared as per Example 54 from the intermediate 5'-O-(4,4'-dimethoxytrityl)-2'-O-propyluridine (470 mg) to yield the product as a foam (477 mg).

Example 62

2'-O-Nonyluridine

As per the procedure of Example 49, uridine (22.5 g) was treated with dibutyl tin oxide (22.5 g, 1 eq). The resulting 2',3'-O-dibutylstannyleneuridine was treated with iodononane (11 ml, 1.3 eq.) at 130–140° C. as per Example 50 to give the 2' and 3' isomers (11.2 g) as an oil.

Example 63

5'-O-(4,4'-Dimethoxytriphenylmethyl)-2'-O-nonyluridine

The mixture of 2'-O-nonyluridine and 3'-O-nonyluridine (11.2 g) was reacted with dimethoxytrityl chloride (10.5 g) as per Example 51. The residue was chromatographed on silica gel eluted with Hex/EtOAc (3:1→1:1 with 1% triethylamine). The appropriate fractions were combined, evaporated under reduced pressure and dried to provide 5.2 g of a foam. An analytical sample was rechromatographed using toluene/EtOAc (3:1 with 1% triethylamine) Anal. Calcd. for C$_{39}$H$_{48}$N$_2$O$_8$: C, 69.62; H, 7.19; N, 4.16. Found: C, 69.66; H, 7.18; N, 4.06.

Example 64

5'-O-(4,4,-dimethoxytriphenylmethyl)-2'-O-nonyluridine-3'-O-(β-cyanoethyl N,N-diisopropylphosphoramidite)

The product was prepared as per Example 54 from the intermediate 5'-O-(4,4'-dimethoxytrityl)-2'-O-nonyluridine (3.1 g) to yield the product as a foam (2.49 g).

Example 65

2'-O-Hexenyluridine

As per the procedure of Example 49, uridine (10.5 g) was treated with dibutyl tin oxide (10.5 g, 1 eq). The resulting 2',3'-O-dibutylstannyleneuridine was treated with 6-bromohexene (3.5 ml, 1.2 eq.) and sodium iodide (3.3 g, 1.0 eq.) at 115° C. as per Example 50 to give the 2' and 3' isomers (3.3 g) as a foam.

Example 66

5'-O-(4,4'-Dimethoxytriphenylmethyl)-2'-O-hexenyluridine

The mixture of 2'-O-hexenyluridine and 3'-O-hexenyluridine (3.1 g) was reacted with dimethoxytrityl chloride (3.5 g, 1.1 eq.) as per Example 51. The residue was chromatographed on silica gel eluted with Hex/EtOAc (3:1→1:1 with 1% triethylamine). The appropriate fractions were combined, evaporated under reduced pressure and dried to provide 2.3 g of a white foam. Anal. Calcd. for C$_{36}$H$_{40}$N$_2$O$_8$·½H$_2$O: C, 67.80; H, 6.48; N, 4.39. Found: C, 68.77; H, 6.41; N, 4.45.

Example 67

5'-O-(4,4'-Dimethoxytriphenylmethyl)-2'-O-hexenyluridine-3'-O-(β-cyanoethyl N,N-diisopropylphosphoramidite)

The product is prepared as per Example 54 from the intermediate 5'-O-(4,4'-dimethoxytrityl)-2'-O-hexenyluridine.

Example 68

5-O-Dimethoxytrityl-2'-O-[hexyl-ω-(N-phthalimido)]uridine-3'-O-(β-cyanethyl N,N-diisopropylphosphoramidite)

In a like manner as per Examples 50 through 52, using N-(6-bromohexyl)phthalimide, an N-phthalimide substituted hexyl group was introduced at the 2'-position of uridine followed by dimethoxytritylation and phosphitylation to give the title nucleotide.

Example 69

5'-Dimethoxytrityl-2-O-[decyl-ω-(N-phthalimido)]uridine-3-O-(β-cyanoethyl N,N-diisopropylphosphoramidite)

In a like manner as per Examples 50 through 52, using N-(10-bromodecyl)phthalimide, an N-phthalimide substituted decyl group was introduced at the 2'-position of uridine followed by dimethoxytritylation and phosphitylation to give the title nucleotide.

Example 70

N4-Benzoyl-2'-O-methylcytidine, Method A

Step 1. 3',5'-O-[(1,1,3,3-Tetraisopropyl)-1,3-disiloxanediyl] cytidine

With stirring, cytidine (40 g, 0.165 mol) and 1,3-dichloro-1,1,3,3-tetraisopropyldisiloxane (TIPS-Cl, 50 g, 0.159 mol) were added to dry pyridine (250 mL). After stirring for 16 h at 25° C., the reaction was concentrated under reduced pressure to an oil. The oil was dissolved in methylene chloride (800 mL) and washed with sat'd sodium bicarbonate (2×300 mL). The organic layer was passed through a silica gel (200 g) scrub column. The product was recovered by elution with methylene chloride-methanol (97:3). The appropriate fractions were combined, evaporated under reduced pressure and dried at 25° C./0.2 mmHg for 1 h to give 59.3 g (77%) of oil. TLC purity 95% (Rf 0.59, ethyl acetate-methanol 9:1). The product may be crystallized from ethyl acetate as white crystals, mp 242–244° C. 41 PMR (DMSO) d 7.7 (H-6), 5.68 (H-5), 5.61 (HO-2'), 5.55 (H-1').

Step 2. N4-Benzoyl-3'-5'-O-[(1,1,3,3)tetraisopropyl-1,3-disiloxanediyl]cytidine

Benzoyl chloride (18.5 g, 0.13 mol) was added over 30 min to a stirred solution of 3',5'-O-[(1,1,3,3-tetraisopropyl)-1,3-disiloxanediyl]cytidine (58 g, 0.12 mol) and triethylamine (15.6 g, 0.16 mol) in dimethylacetamide (400 mL) at 5° C. The mixture was allowed to warm to 25° C. for 16 h and then poured onto ice water (3.5 L) with stirring. The resulting solid was collected, washed with ice water (3×500 mL) and dried at 45° C./0.2 mmHg for 5 h to provide 77 g (100%) of solid. TLC purity ca. 90% (Rf 0.63, chloroform-methanol 9:1); PMR (CDCL$_3$) d 8.32 (H-6); mp 100–101° C.

Step 3. N4-Benzoyl-2'-O-methyl-3',5'-O-[(1,1,3,3) tetraisopropyl-1,3-disiloxanediyl]cytidine A mixture of N4-benzoyl-3'-5'-O-[(1,1,3,3)tetraisopropyl-1,3-disiloxanediyl]cytidine (166 g, 0.25 mol, 90% purity), silver oxide (150 g, 0.65 mol) and toluene (300 mL) was evaporated under reduced pressure. More toluene (500 mL) was added and an additional amount (100 mL) was evaporated. Under a nitrogen atmosphere, methyl iodide was added in one portion and the reaction was stirred at 40° C. for 16 h. The silver salts were collected and washed with ethyl acetate (3×150 mL). The combined filtrate was concentrated under reduced pressure. The residue was dissolved in a minimum of methylene chloride, applied to a silica gel column (1 kg) and eluted with hexanes-ethyl acetate (3:2→1:1). The appropriate fractions were combined, concentrated under reduced pressure and dried at 45° C./0.2 mmHg for 1 h to yield 111 g (66%) of oil; TLC purity ca. 90% (Rf 0.59, hexanes-ethyl acetate 3:2). PMR (CDCl$_3$) d 8.8 (br s, 1, H—N$^4$), 8.40 (d, 1, H-6), 8.0–7.4 (m, 6, H-5 and Bz), 5.86 (s, 1, H-1'), 3.74 (s, 3, CH$_3$O-2').

Step 4. N4-Benzoyl-2'-O-methylcytidine

A solution of N4-benzoyl-2'-O-methyl-3',5'-O-[(1,1,3,3) tetraisopropyl-1,3-disiloxanediyl]cytidine (111 g, 0.18 mol) in methanol (160 mL) and tetrahydrofuran (640 mL) was, treated with tetrabutylammonium fluoride solution (368 mL, 1 M in tetrahydrofuran). The reaction was stirred at 25° C. for 16 h. The pH was adjusted to 7 with Amberlite IRC-50 resin. The mixture was filtered and the resin was washed with hot methanol (2×200 mL). The combined filtrate was concentrated under reduced pressure, absorbed on silica gel (175 g) and chromatographed on silica gel (500 g, ethyl acetate-methanol. 19:1→4:1). Selected fractions were combined, concentrated under reduced pressure and dried at 40° C./0.2 mmHg for 2 h to yield 28 g (42.4%, 21.5% from cytidine) of solid; TLC: homogenous (Rf 0.37, ethyl acetate). mp 178–180° C. (recryst. from ethanol); PMR (CDCl$_3$) d 11.22 (br s, 1, H—N$^4$), 8.55 (d, 1, H-6), 8.1–7.2 (m, 6, H-5 and Bz), 5.89 (d, 1, H-1'), 5.2 (m, 2, HO-3',5'), 3.48 (s, 3, CH$_3$O-2').

Example 71

N4-Benzoyl-2'-O-methylcytidine, Method B

Step 1. 2'-O-methylcytidine

Cytidine (100 g, 0.41 mol) was dissolved in warm dimethylformamide (65° C., 1125 mL). The solution was cooled with stirring to 0° C. A slow, steady stream of nitrogen gas was delivered throughout the reaction. Sodium hydride (60% in oil, washed thrice with hexanes, 18 g, 0.45 mol) was added and the mixture was stirred at 0° C. for 45 min. A solution of methyl iodide (92.25 g, 40.5 mL, 0.65 mol) in dimethylformamide (400 mL) was added in portions over 4 h at 0° C. The mixture was stirred for 7 h at 25° C. and then filtered. The filtrate was concentrated to dryness under reduced pressure followed by co-evaporation with methanol (2×200 mL). The residue was dissolved in methanol (350 mL). The solution was adsorbed on silica gel (175 g) and evaporated to dryness. The mixture was slurried in dichloromethane (500 mL) and applied on top of a silica gel column (1 kg). The column was eluted with a gradient of dichloromethane-methanol (10:1→2:1). The less polar 2',3'-dimethyl side product was removed and the co-eluting 2' and 3'-O-methyl product containing fraction were combined and evaporated under reduced pressure to a syrup. The syrup was dissolved in a minimum of hot ethanol (ca. 150 mL) and allowed to cool to 25° C. The resulting precipitate (2' less soluble) was collected, washed with ethanol (2×25 ml) and dried to give 15.2 g of pure 2'-O-methylcytidine; mp 252–254° C. mp 252–254° C.); TLC homogenous (Rf 0.50, dichloromethane-methanol 3:1, (Rf of 3' isomer 0.50 and the dimethyl product 0.80). The filtrate was evaporated to give 18 g of a mixture of isomers and sodium iodide.

Step 2. N4-Benzoyl-2'-O-methylcytidine

The pure 2'-O-methylcytidine (15.2 g, 0.060 mol) was dissolved in a solution of benzoic anhydride (14.7 g, 0.12 mol) in dimethylformamide (200 mL). The solution was stirred at 25° C. for 48 h and then evaporated to dryness under reduced pressure. The residue was triturated with methanol (2×200 mL), collected and then triturated with warm ether (300 mL) for 10 min. The solid was collected and triturated with hot 2-propanol (50 mL) and allowed to stand at 4° C. for 16 h. The solid was collected and dried to give 17 g of product. The crude filtrate residue (18 g) of 2'-O-methylcytidine was; treated with benzoic anhydride (17.3 g, 0.076 mol) in dimethylformamide (250 mL) as above and triturated in a similar fashion to give an additional 6.7 g of pure product for a total yield of 23.7 g (16% from cytidine) of solid; TLC homogenous (Rf 0.25, chloroform-methanol 5:1, co-spots with material made utilizing Method A)

Example 72

N4-Benzoyl-5'-O-(4,4'-dimethoxytriphenylmethyl)-2'-O-methylcytidine

N4-Benzoyl-2'-O-methylcytidine, (28 g, 0.077 mol) was evaporated under reduced pressure to an oil with pyridine (400 mL). To the residue was added 4,4'-dimethoxytriphenylmethyl chloride (DMT-Cl, 28.8 g, 0.085 mol) and pyridine (400 mL). The mixture was stirred at 25° C. for 2 h and then quenched by the addition of methanol (10 mL) for 30 min. The mixture was concentrated under reduced pressure and the residue was chromatographed on silica gel (500 g, hexanes-ethyl acetate-triethylamine 60:40:1 and then ethyl acetate-triethylamine 99:1). The appropriate fractions were combined, evaporated under reduced pressure and dried at 40° C./0.2 mmHg for 2 h to give 26 g (74%) of foam; TLC homogenous (Rf 0.45, ethyl acetate); PMR (DMSO) d 11.3 (H—N$^4$), 8.4–6.9 (H-6, H-5, Bz), 5.95 (H-1'), 5.2 (HO-3'), 3.7 (s, 6, CH$_3$O-trit.), 3.5 (s, 3, CH$_3$O-2')

Example 73

N4-Benzoyl-5'-O-(4,4'-dimethoxytriphenylmethyl)-2'-O-methylcytidine-3'-O-(β-cyanoethyl N,N-diisopropylphosphoramidite)

The product was prepared as per the procedure of Example 38 starting with intermediate compound N4-benzoyl-5'-O-(4,4'-dimethoxytriphenylmethyl)-2'-O-methylcytidine (22.0 g, 0.0333 mole) and using ethyl acetate-hexanes-triethylamine (59:40:1) as the chromatography eluent to give the product as a solid foam (23.6 g) in 83% yield; TLC homogenous diastereomers (Rf 0.46; 0.33, ethyl acetate-hexanes-triethylamine 59:40:1); $^{31}$P-NMR (CD$_3$CN, H$_3$PO$_4$ std.) d 150.34; 151.02 (diastereomers).

Example 74

2'-O-Nonylcytidine

Cytidine (10.1 g, 0.0415 mol), sodium hydride (2.0 g, 1.2 eq), iodononane (9.8 ml, 1.2 eq.) in DMF (100 ml) were reacted as per the procedure of Example 71, Step 1 to yield the 2' and 3' isomers as a sticky foam (11.6 g).

Example 75

N4-Benzoyl-2'-O-nonylcytidine

The mixture of 2'-O-nonylcytidine and 3'-O-nonylcytidine (11.5 g) is converted to N4-benzoyl-2'-O-nonylcytidine as per the procedure of Example 71, Step 2.

Example 76

N4-Benzoyl-5'-O-(dimethoxytrityl)-2'-O-nonylcytidine

N4-Benzoyl-2'-O-nonylcytidine (2.67 g, 0.0056 mol) was treated with dimethoxytrityl chloride (2.0 g, 1.1 eq) as per the procedure of Example 72 to give 4.2 g of pure product. Anal. Calcd. for C$_{46}$H$_{53}$N$_3$O$_8$·½H$_2$O: C, 70.39; H, 6.93; N, 5.35. Found: C, 71.20; H, 6.88; N, 5.41.

Example 77

N4-Benzoyl-5'-O-(dimethoxytrityl)-2'-O-nonylcytidine-3'-O-(β-cyanoethyl N,N-diisopropylphosphoramidite)

The product was prepared as per the procedure of Example 38 starting with intermediate compound N4-benzoyl-5'-O-(4,4'-dimethoxytriphenylmethyl)-2'-O-nonylcytidine (4.1 g, 0.0053 mole) treated with bis-N,N-diisopropylaminocyanoethylphosphite (3.3 ml) and N,N-diisopropylaminohydrotetrazolide (450 mg). The product was eluted from the silica gel column using Hexane/EtOAc (3:1→1:1 with 1% triethylamine) as the chromatography eluent to give the product as a solid foam (4.21 g). $^{31}$P-NMR (CD$_3$CN, H$_3$PO$_4$ std.) shows the diastereomers;

Example 78

2'-O-Pentylcytidine

Cytidine (10 g, 0.041 mol), sodium hydride (2.4 g, 1.5 eq), bromopentane (7.6 ml, 1.5 eq.) in DMSO (90 ml) were reacted as per the procedure of Example 71, Step 1 to yield the 2' and 3' isomers as a foam (7.6 g).

Example 79

N4-Benzoyl-2'-O-pentylcytidine

The mixture of 2'-O-pentylcytidine and 3'-O-pentylcytidine (7.5 g) is converted to N4-benzoyl-2'-O-pentylcytidine as per the procedure of Example 71, Step 2.

Example 80

N4-Benzoyl-5'-O-(dimethoxytrityl)-2'-O-pentylcytidine

N4-Benzoyl-2'-O-pentylcytidine (3.0 g, 0.007 mol) was treated with dimethoxytrityl chloride (2.7 g, 1.1 eq) as per the procedure of Example 72 to give 3.5 g of pure product. Anal. Calcd. for C$_{42}$H$_{45}$N$_3$O$_8$·½H$_2$O: C, 69.21; H, 6.36; N, 5.76. Found: C, 69.51; H, 6.30; N. 5.71.

Example 81

N4-Benzoyl-5'-O-(dimethoxytrityl)-2'-O-pentylcytidine-3'-O-(β-cyanoethyl N,N-diisopropylphosphoramidite)

The product was prepared as per the procedure of Example 38 starting with intermediate compound N4-benzoyl-5'-O-(4,4'-dimethoxytriphenylmethyl)-2'-O-pentylcytidine (3.5 g, 0.0048 mole) treated with bis-N,N-diisopropylaminocyanoethylphosphite (2.9 g, 3.1 ml, 2 eq.) and N,N-diisopropylaminohydrotetrazolide (400 mg, 0.5 eq.). The product was eluted from the silica gel column using Hexane/EtOAc (3:1→1:1 with 1% triethylamine) as the chromatography eluent to give the product as a solid foam (3.24 g). $^{31}$P-NMR (CD$_3$CN, H$_3$PO$_4$ std.) shows the diastereomers.

Example 82

2'-O-Propylcytidine

Cytidine (16.5 g, 0.068 mol) was treated with sodium hydride (4.5 g) and bromopropane (15 ml) in DMF (150 ml) at room temperature for three days. The resulting reaction mixture was used directly in the next step (see Example 83).

Example 83

N4-Benzoyl-2'-O-propylcytidine

To the 2'-O-propylcytidine reaction mixture of Example 82 in an ice bath was added pyridine (60 ml) and trimethylsilyl chloride (60 ml). The reaction was stirred for 30 mins followed by the addition of benzoyl chloride (55 ml). The resulting reaction mixture was stirred for 2.5 hrs and then cooled in an ice bath. H$_2$O (100 ml) and conc. NH$_4$OH (100 ml) were added. After stirring for 30 mins, the reaction mixture was evaporated and the residue partition between H$_2$O and CH$_2$Cl$_2$. The organic phase was washed once with dil Na$_2$CO$_3$, once with dil HCl, dried over MgSO$_4$ and evaporated. The resulting residue was loaded on a silica gel column (150 g) and eluted with first CH$_2$Cl$_2$ then 5 to 10% MeOH in CH$_2$Cl$_2$ as the elution solvent. The product containing fractions were evaporated to a foam. The foam was crystallized from EtOAc/Hexanes to give the product (6.5 g total) in several crystal batches.

Example 84

N4-Benzoyl-5'-O-(dimethoxytrityl)-2'-O-propylcytidine

N4-Benzoyl-2'-O-propylcytidine (3.0 g, 0.007 mol) was treated with dimethoxytrityl chloride (1.5 g) as per the procedure of Example 72 to give 1.5 g of pure product. Anal. Calcd. for C$_{40}$H$_{42}$N$_3$O$_8$·½H$_2$O: C, 68.45; H, 6.18; H, 5.99. Found: C, 68.39; H, 5.99; N, 5.95.

Example 85

N4-Benzoyl-5'-O-(dimethoxytrityl)-2'-O-propylcytidine-3'-O-(β-cyanoethyl N,N-diisopropylphosphoramidite)

The product was prepared as per the procedure of Example 38 starting with intermediate compound N4-benzoyl-5'-O-(4,4'-dimethoxytriphenylmethyl)-2'-O-propylcytidine (3.8 g, 0.0055 mole) treated with bis-N,N-diisopropylaminocyanoethylphosphite (3.5 ml, 2 eq.) and N,N-diisopropylaminohydrotetrazolide (500 mg, 0.5 eq.). The product was eluted from the silica gel column using Hexane/EtOAc (1:1 with 1% triethylamine) as the chromatography eluent to give the product as a solid foam (4.72 g). $^{31}$P-NMR (CD$_3$CN, H$_3$PO$_4$ std.) shows the diastereomers.

Example 86

N2,N6-Diisobutyrylamino-9-(2'-O-methyl-β-D-ribofuranosyl)purine

N2, N6-Diamino-9-(2'-O-methyl-β-D-ribofuranosyl) purine (1.6 g, 5.39 mmol, see Example 34) was co-evaporated with pyridine (25 ml). A suspension of the residue in pyridine (40 ml) was cooled in an ice bath and trimethylsilyl chloride (4.8 ml) was added. The reaction mixture was stirred for 30 mins followed by the addition of butyryl chloride (2.8 ml, 5 eq). The resulting reaction mixture was stirred at room temperature for 4 hours. H$_2$O (10 ml) and conc. NH$_4$OH (10 ml) were added with stirring to quench the reaction mixture. After 30 mins, the reaction mixture was evaporated and the residue purified on a silica gel column using CH$_2$Cl$_2$→10% MeOH/CH$_2$Cl$_2$ to elute the product. The appropriate fractions were evaporated to yield the product as an oil (2.4 g).

Example 87

N2,N6-Diisobutyrylamino-9-(5'-O-dimethoxytrityl-2'-O-methyl-β-D-ribofuranosyl)purine N2,N6-Diisobutyrylamino-9-(2'-O-methyl-β-D-ribofuranosyl)purine (2.4 g) was co-evaporated with pyridine and redissolved in pyridine. Dimethoxytrityl chloride (1.8 g, 1 eq) and dimethylaminopyridine (5 mg) were added and the resulting solution was stirred overnight at room temperature. The solvent was partly evaporated and the residue partition between CH$_2$Cl$_2$—dil. Na$_2$CO$_3$. The organic phase was washed with dil. Na$_2$CO$_3$, dried with MgSO$_4$ and evaporated. The residue was purified on a silica gel column eluted with Hexanes/EtOAc (1:1) containing 1% triethylamine. The fraction contain the product were evaporated to yield the product as a foam (2.4 g).

Example 88

N2,N6-Diisobutyrylamino-9-[5'-O-dimethoxytrityl-2'-O-methyl-3'-O-(β-cyanoethyl N,N-diisopropylphosphoramide)-β-D-ribofuranosyl] purine N2,N6-Diisobutyrylamino-9-(5'-O-dimethoxytrityl-2'-O-methyl-β-D-ribofuranosyl)purine (1.7 g, 0.0023 mol) was treated with bis-N,N-diisopropylaminocyanoethylphosphite (1.48 ml, 2 eq.) and N,N-diisopropylaminohydrotetrazolide (200 mg) at room temperature overnight. The reaction mixture was partitioned between dil. Na$_2$CO$_3$/CH$_2$Cl$_2$, the organic phase was dried over MgSO$_4$ and evaporated. The residue was loaded on a silica gel column and eluted with Hexanes/EtOAc (3:1→1:1 with 1% triethylamine) to give the product as a solid foam (1.73 g). $^{31}$P-NMR (CD$_3$CN, H$_3$PO$_4$ std.) shows the diastereomers.

Example 89

Oligonucleotide Synthesis

Once nucleoside phosphoramidites of the invention have been prepared, they can then subsequently be incorporated into oligonucleotides, which are synthesized by a standard solid phase, automated nucleic acid synthesizer such as the Applied Biosystems, Incorporated 380B or MilliGen/Biosearch 7500 or 8800. Standard phosphoramidite coupling chemistries (see, e.g., M. Caruthers, *Oligonucleotides. Antisense Inhibitors of Gene Expression.*, pp. 7–24, J. S. Cohen, ed., CRC Press, Inc. Boca Raton, Fla., 1989) are used with these synthesizers to provide the desired oligonucleotides. The Beaucage reagent (see, e.g., *J. Am. Chem. Soc.* 1990, 112, 1253) or elemental sulfur (see, e.g., *Tetrahedron Letters* 1981, 22, 1859), can likewise be used to provide phosphorothioate oligonucleotides.

We claim:

1. A process for preparing a 2'-O-alkylated cytidine 3'-O-phosphoramidite comprising the steps of:

alkylating an unblocked cytidine to form a 2'-O-alkylated cytidine;

blocking the 5'-hydroxyl moiety of said 2'-O-alkylated cytidine; and phosphitylating the 3'-position of said 5'-blocked 2'-O-alkylated cytidine.

2. The process of claim 1 wherein said alkylation is in the presence of base.

3. The process of claim 2 wherein said base is a metal hydride.

4. The process of claim 1 wherein said blocking step adds a dimethoxytrityl group.

5. The process of claim 1 wherein said phosphitylation step is conducted with bis-N,N-diisopropylaminocyanoethylphosphite.

6. The process of claim 5 wherein said phosphitylation step is conducted in the presence of N,N-diisopropylaminohydrotetrazolide.

7. The process of claim 1 further comprising blocking the N4-amino moiety of said 2'-O-alkylated cytidine prior to blocking said 5' hydroxyl moiety.

* * * * *